United States Patent
Dominianni et al.

(10) Patent No.: US 6,194,446 B1
(45) Date of Patent: Feb. 27, 2001

(54) HYPOGLYCEMIC AND HYPOLIPIDEMIC COMPOUNDS

(75) Inventors: Samuel James Dominianni, Indianapolis; Margaret Mary Faul, Zionsville; Russell Dean Stucky, Indianapolis; Leonard Larry Winneroski, Jr., Greenwood, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/216,471

(22) Filed: Dec. 18, 1998

Related U.S. Application Data

(63) Continuation of application No. PCT/US97/11576, filed on Jun. 30, 1997
(60) Provisional application No. 60/021,016, filed on Jul. 1, 1996.

(51) Int. Cl.$^7$ ........................ C07D 263/32; A61K 31/421
(52) U.S. Cl. ........................ 514/374; 548/236; 548/235
(58) Field of Search ................................ 548/236, 235; 514/374

(56) References Cited

U.S. PATENT DOCUMENTS

| | | |
|---|---|---|
| 4,954,512 | 9/1990 | Oguro et al. . |
| 5,036,079 | 7/1991 | Clark et al. . |
| 5,236,934 | 8/1993 | VanAtten . |
| 5,246,943 | 9/1993 | Blankley et al. . |
| 5,306,726 | 4/1994 | Hulin . |
| 5,312,923 | 5/1994 | Chung et al. . |
| 5,350,757 | 9/1994 | Blankley et al. . |
| 5,480,891 | 1/1996 | Yamasaki et al. . |
| 5,491,159 | 2/1996 | Malamas . |
| 5,525,614 | 6/1996 | Blankley et al. . |
| 5,648,368 * | 7/1997 | Egbertson ............... 514/331 |

FOREIGN PATENT DOCUMENTS

| | | |
|---|---|---|
| 317959 | 11/1988 | (EP) . |
| 478328A1 | 9/1991 | (EP) . |
| 478363A2 | 9/1991 | (EP) . |
| 528587A1 | 8/1992 | (EP) . |
| 558139A1 | 2/1993 | (EP) . |
| 728469A2 | 2/1996 | (EP) . |
| WO 92/21342 | 12/1992 | (WO) . |
| WO 93/16994 | 9/1993 | (WO) . |
| WO 93/23409 | 11/1993 | (WO) . |
| WO 94/12181 | 6/1994 | (WO) . |
| WO 94/13650 | 6/1994 | (WO) . |
| WO 94/29285 | 12/1994 | (WO) . |
| WO 94/29302 | 12/1994 | (WO) . |
| WO 96/38415A1 | 12/1996 | (WO) . |

OTHER PUBLICATIONS

Gerich, J.E., New Engl. J. Med., 321, 1231–1245 (1989).
Diabetes Care, 18, Supplement 1, 86–93 (1995).
Burger's Medicinal Chemistry, 4$^{th}$ Ed., Part II, John Wiley and Sons, N.Y., 1979, 1057–1080.
Ellingboe, et al., J. Med. Chem. 36, 2485–2493 (1993).
Colca, J.R., and Morton, D.R., New Antidiabetic Drugs, ed. C.J. Bailey and P.R. Flatt, Smith–Gordon Company, Ltd., London, Chapter 24 (1990).
Sato, Y., et al., Diabetes Research and Clinical Practice, 12, 53–60 (1991).
J. Med. Chem. 38, 695–707 (1995).

* cited by examiner

*Primary Examiner*—Robert Gerstl
(74) *Attorney, Agent, or Firm*—Francis O. Ginah; Paul R. Darkes

(57) ABSTRACT

This invention provides compounds and their pharmaceutically-acceptable salts, pharmaceutical formulations of said compounds, and methods for treating hyperglycemia associated with non-insulin dependent diabetes and for treating hyperlipidemia.

30 Claims, No Drawings

HYPOGLYCEMIC AND HYPOLIPIDEMIC COMPOUNDS

This application is a continuation of International Application No. PCT/US97/11576, filed Jun. 30, 1997, which, in turn, claims the benefit of U.S. Provisional Application No. 60/021,016, filed Jul. 1, 1996.

This invention relates to the treatment and control of hyperglycemia, such as occurs in non-insulin-dependent diabetes mellitus (NIDDM). This invention also relates to treatment and control of hyperlipidemia.

BACKGROUND OF THE INVENTION

The disease, diabetes mellitus, is recognized in two forms. Type I diabetes requires exogenous insulin for control of the disease because it appears that endogenous production of insulin by the Isles of Langerhans in the pancreas is extremely poor or non-existent. Type I diabetes is often referred to as insulin-dependent diabetes mellitus (IDDM). Type II, non-insulin-dependent diabetes mellitus (NIDDM), is characterized by defects of insulin sensitivity in peripheral tissues such as adipose tissue and muscle, as described by J. E. Gerich in *New Engl. J. Med.*, 321, 1231–1245 (1989).

Hyperlipidemia is often observed in diabetics (*Diabetes Care*, 18, Supplement 1, 86–93, 1995). The combination of hyperlipidemia and hyperglycemia greatly increases the risk of cardiovascular diseases in diabetics. Successful treatment of hyperlipidemia and hyperglycemia in diabetics is needed urgently.

Blank reviewed hypoglycemic agents (*Burger's Medicinal Chemistry*, 4th Ed., Part II, John Wiley and Sons, N.Y., 1979, 1057–1080). Newer hypoglycemic agents were reviewed by Hulin in *Progress in Medicinal Chemistry*, 31, ed. G. P. Ellis and D. K. Luscombe, Elsevier Publishing Co., 1993.

Currently, partial control of NIDDM is achieved by a diet and exercise regimen, by administration of exogenous insulin, by administration of hypoglycemic agents, (e.g. the sulfonylureas), or by some combination of these protocols. Sulfonylureas, such as chloropropamide, acetohexamide and tolbutamide, are useful orally-effective hypoglycemic agents achieving success in the control of NIDDM in numbers of patients. However, drugs currently available for the control of the hyperglycemia associated with type II diabetes mellitus (NIDDM) possess significant liabilities or limitations of efficacy. (Ellingboe, et al., *J. Med. Chem.* 36:2485–2493, 1993). Considerable effort has been expended toward developing novel, orally-administered antihyperglycemic drugs. A preferred therapeutic approach for treating NIDDM incorporates drugs that counteract insulin resistance rather than those that stimulate endogenous insulin secretion. (J. R. Colca and D. R. Morton, *New Antidiabetic Drugs*, ed. C. J. Bailey and P. R. Flatt, Smith-Gordon and Company, Ltd., London, Chapter 24, 1990). Drugs that treat insulin resistance are called insulin sensitivity enhancers.

Sato, Y, et al. (*Diabetes Research and Clinical Practice*, 12:53–60, 1991) described the hypoglycemic effect of D-phenylalanine derivatives. In normal dogs, the hypoglycemic activity of the compound was greater than that of tolbutamide but less than that of glibenclamide. The compounds exerted a rapid hypoglycemic effect and improved glucose tolerance in genetically diabetic KK mice and in streptozotocin-treated rats. Yamasaki, et al., disclosed a group of 2-quinolone derivatives showing antidiabetic activity in NIDDM (WO 92/21342).

Some known hypoglycemic compounds also reduce serum cholesterol or triglyceride levels. (Clark, et al., U.S. Pat. No. 5,036,079). The combination of these biological activities in one compound is particularly advantageous because diabetics are highly susceptible to hyperlipidemia. Hulin, in U.S. Pat. No. 5,306,726, claimed phenylpropionic acid derivatives and disclosed compounds that had hypoglycemic and hypocholesterolemic activity useful for the treatment of diabetes and atherosclerosis. Miyata, et al. found a class of phosphonic diester derivatives useful for treating diabetes and hyperlipidemia (WO 93/23409). Hypolipidemic amino acid derivatives were disclosed in JA-028189. Highly substituted aryl ethers of tyrosine were reported to have hypocholesterolemic activity (*J. Med. Chem.*, 38:695–707, 1995). No aklyl ethers of tyrosine were disclosed.

SUMMARY OF THE INVENTION

This invention provides compounds of the Formula I

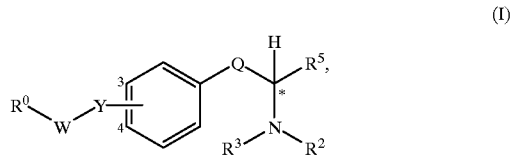

wherein:

Q is selected from the group consisting of $-(CH_2)_p-$ and $-CH_2-O-CH_2-$;

$R^0$ is selected from the group consisting of

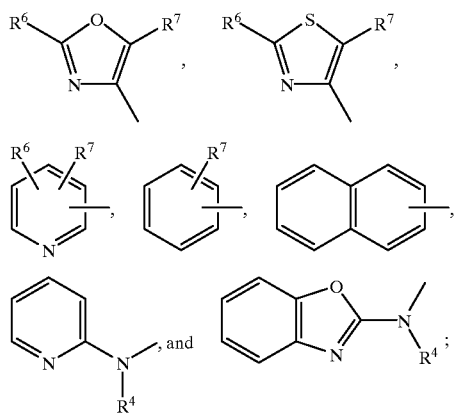

$R^2$ is selected from the group consisting of $C_{1-4}$ alkylaminocarbonyl, arylcarbonyl, aryloxycarbonyl, aryloxy $C_{1-4}$ alkylcarbonyl, arylaminocarbonyl, aryl $C_{1-4}$ acyl, aryl $C_{1-4}$ alkoxycarbonyl, aryl $C_{1-4}$ alkylaminocarbonyl, aryl $C_{1-4}$ alkylsulfonyl and amino protecting groups;

$R^3$ and $R^4$ are independently hydrogen, or $C_{1-4}$ alkyl;

$R^5$ is —COOH, —CONR$^{10}$R$^{11}$, —CN, —CONHOH, or

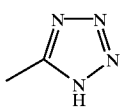

$R^6$ is hydrogen, $C_{1-4}$ alkyl, aryl, or aryl $C_{1-4}$ alkyl;
$R^7$ is hydrogen, halogen, or $C_{1-4}$ alkyl;
$R^9$ is hydrogen, $C_{1-4}$ alkyl, or aryl;
$R^{10}$ and $R^{11}$ are independently hydrogen, $C_{1-4}$ alkyl, or aryl;
W is —(CH$_2$)$_n$—;
Y is attached at position 3 or at position 4 or the ring, and is —O—, —S—, —SO—, —SO$_2$—, —NH—, —CONR$^9$—, —NR$^9$—SO$_2$—, or —SO$_2$—NR$^9$—;
n is 1 to 4; and
p is 1, 2, or 3;
or a pharmaceutically-acceptable salt thereof;
provided that when $R^6$ is either hydrogen or $C_{1-4}$ alkyl, then $R^7$ is halogen, and that when p=1, then $R^0$ is

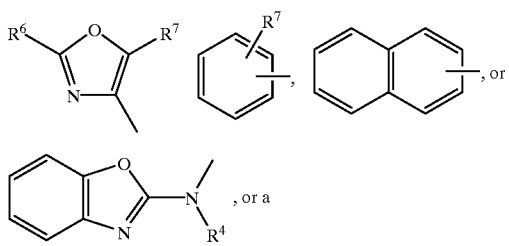

or a pharmaceutically acceptable salt thereof.

This invention also provides pharmaceutical formulations of the compounds of Formula I, and methods for treating hyperglycemia associated with non-insulin dependent diabetes and for treating hyperlipidemia by administering to a mammal an effective dose of a compound of the Formula I.

DETAILED DESCRIPTION

The terms used to describe the instant invention have the following meanings herein.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

"Halogen" refers to fluoro, chloro, bromo or iodo.

"$C_{1-4}$ alkyl" refers to straight or branched alkyl radicals having 1 to 4 carbon atoms, for example, methyl, ethyl, n-propyl, iso-propyl, n-butyl, sec-butyl, and t-butyl.

"$C_{1-4}$ alkoxy" refers to straight or branched chain alkyl radicals attached to oxygen having 1 to 4 carbon atoms, for example, methoxy, ethoxy, n-propoxy, iso-propoxy, t-butoxy, and the like.

"$C_{1-4}$ alkylaminocarbonyl" refers to radicals of the formula:

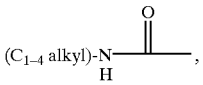

and includes, for example, methylaminocarbonyl, ethylaminocarbonyl, 2-propylaminocarbonyl, and the like.

"Aryl" refers to a substituted or unsubstituted aromatic radical selected from the group consisting of 2-furyl, 3-furyl, 2-thienyl 3-thienyl, 1-pyrrolyl, 2-pyrrolyl, 3-pyrrolyl, phenyl, 2-pyridyl, 3-pyridyl, 4-pyridyl, 1-naphthyl, 2-naphthyl, 2-benzofuryl, 3-benzofuryl, 4-benzofuryl, 5-benzofuryl, 6-benzofuryl, 7-benzofuryl, 2-benzothieny, 3-benzothieny, 4-benzothieny, 5-benzothieny, 6-benzothieny, 7-benzothienyl, 1indolyl, 2-indolyl, 3-indolyl, 4-indolyl, 5-indolyl, 6-indolyl, 7-indolyl, and 8-indolyl. The optional substitutions of aryl may be at one or two carbon atoms of the aryl group, and may be with $C_{1-4}$ alkyl, $C_{1-4}$ alkoxy, halogen, —NO$_2$, —CN, —COOH, —CONH$_2$, —SO$_3$H, —SO$_2$NH$_2$ or trifluoromethyl. Examples of substituted aryl groups are 4-methyl-3-furyl, 3,4-dimethyl-2-thienyl, 2,4-dimethyl-3-thienyl, 3-ethoxy-4-methyl-2-benzofuryl, 2-cyano-3-benzofuryl, 4-trifluoromethyl-2-benzothienyl, 2-chloro-3-benzothienyl, 3,4-dichloro-2-pyridyl, 2-bromo-3-pyridyl, 2-fluoro-4-pyridyl, 4-fluoro-2-furyl, 2-carboxyphenyl, 4-carboxamidophenyl, 3-trifluoromethylphenyl, bromo-1-naphthyl, 2,3-dimethyl-1-naphthyl, 3-carboxy-2-naphthyl, 5-carboxy-8-chloro-1-naphthyl, 3-ethyl-2-furyl, 8-fluoro-2-naphthyl, 5-trifluoromethyl-2-naphthyl, 6-ethoxy-2-naphthyl, 6,7-dimethoxy-2-naphthyl, 3-carboxy-2-naphthyl, and the like.

"Arylcarbonyl" refers to radicals of the formula:

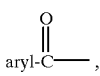

for example, phenylcarbonyl, 4-methyl-1-naphthylcarbonyl, 3-trifluoromethylphenylcarbonyl, and the like.

"Aryloxycarbonyl" refers to radicals of the formula:

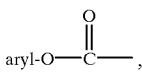

and includes, for example, phenyloxycarbonyl, 1-naphthyloxycarbonyl, 3-benzofuryloxycarbonyl, 2-benzothienyloxycarbonyl, 3-benzothienyloxycarbonyl, 2-pyridyloxycarbonyl, 3-pyridyloxycarbonyl, 3-ethyl-2-furyloxycarbonyl, 8-fluoro-2-naphthyloxycarbonyl, and the like.

"Arylaminocarbonyl" refers to radicals of the formula:

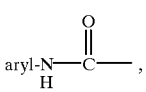

and includes, for example, phenylaminocarbonyl, 2-naphthylaminocarbonyl, 4-methyl-3-furylaminocarbonyl, 3,4-dimethyl-2-thienylaminocarbonyl, 2,4-dimethyl-3-thienylaminocarbonyl, 3-ethoxy-4-methyl-2- benzofurylaminocarbonyl, 2-cyano-3-benzofurylaminocarbonyl, 4-trifluoromethyl-2-benzothienylaminocarbonyl, 2-chloro-3-benzothienylaminocarbonyl, 3,4-dichloro-2-pyridylaminocarbonyl, 2-bromo-3-pyridylaminocarbonyl, 3-furylaminocarbonyl, 2-benzofurylaminocarbonyl, 4-pyridylaminocarbonyl, and the like.

"Aryl $C_{1-4}$ acyl" refers to radicals of the formula:

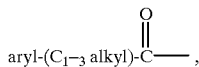

and includes, for example para-trifluoromethylbenzylcarbonyl, phenylacetyl, 2-(1-naphthyl)ethylcarbonyl, 2-phenylethylcarbonyl, 2-(3-benzofuryl)ethylcarbonyl, 2-furylacetyl, and the like.

"Aryl $C_{1-4}$ alkyloxycarbonyl" refers to radicals of the formula:

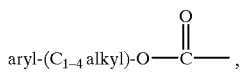

and includes, for example, benzyloxycarbonyl, 2-(2-naphthyl)ethoxycarbonyl, 6-phenylpropoxycarbonyl, 2-benzofurylmethoxycarbonyl, 3-chloro-4-methylbenzyloxycarbonyl, 4-carboxamidobenzyloxycarbonyl, and the like.

"Aryloxy $C_{1-4}$ alkylcarbonyl" refers to radicals of the formula:

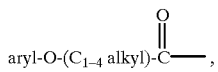

and includes, for example, phenyloxymethylcarbonyl, 2-(2-indoyloxy)ethylcarbonyl, 3-(1-naphthyloxy) propylcarbonyl, 4-(3,5-dimethyl-4-pyridyloxy) butylcarbonyl, and the like.

"Aryl $C_{1-4}$ alkylaminocarbonyl" refers to radicals of the formula:

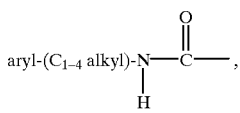

and includes, for example, phenylmethylaminocarbonyl, 2-(2-benzothienyl) propylaminocarbonyl, (2-naphthyl) methylaminocarbonyl, 2-thienylmethylaminocarbonyl, and the like.

"Aryl $C_{1-4}$ alkylsufonyl" refers to radicals of the formula:

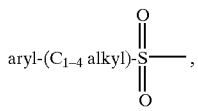

and includes, for example, phenylmethylsulfonyl, and the like.

"Aryl $C_{1-4}$ alkyl" refers to radicals of the formula: aryl—($C_{1-4}$ alkyl)—, and includes, for example, phenylmethyl, 2-(2-theinyl)ethyl, 3-(2-benzofuryl)propyl, benzyl, 4-chlorobenzyl, 3-ethyl-4-methylbenzyl, 3-chloro-4-methylbenzyl, 3,4-dichlorobenzyl, 3-isopropoxybenzyl, and the like.

The term "amino protecting group" as used herein refers to substituents of the amino group commonly employed to block or protect the amino functionality while reacting other functional groups on the compound. Examples of such amino-protecting groups include the formyl group, the phtalimido group, the trichloroacetyl group, the chloroacetyl, bromoacetyl, and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl) ethoxycarbonyl, allyloxycarbonyl, 1-(trimethylsilylmethyl) prop-1-en-3-yloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl, and the like; the benzoylmethylsulfonyl, the 2-(nitro)phenylsulfenyl group, the diphenylphosphine oxide group, and like amino protecting groups. The species of amino protecting group employed is not critical so long as the derivitized amino group is stable to the conditions of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by J. S. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino protecting group discussed above.

The term "carboxy protecting group" as used herein refers to one of the ester derivatives of the carboxylic acid group commonly employed to block or protect the carboxylic acid group while reactions are carried out on other functional groups of the compound. Examples of such carboxylic acid protecting groups include benzyl, 4-nitrobenzyl, 4-methoxybenzyl, 3,4-dimethoxybenzyl, 2,4- dimethoxybenzyl, 2,4,6-trimethoxybenzyl, pentamethylbenzyl, 3,4-methylenediozybenzyl, benzyhydryl, 4,4'-dimethoxybenzhydryl, 2,2,4,4'-tetramethoxybenzhydryl, t-butyl, isobutyl, n-butyl, propyl, isopropyl, ethyl, methyl, t-amyl, trityl, 4-methoxytrityl, 4,4'-dimethoxytrityl, 4,4',4"-trimethoxytrityl, trimethylsilyl, t-butyldimethylsilyl, phenyacyl, 2,2,2-trichloroethyl, B-(trimethylsilyl)ethyl, B-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivitized carboxylic acid is stable to the conditions of subsequent reaction(s) on other positions of the molecule and can be removed at the appropriate point without disrupting the remainder of the molecule. Carboxy protecting groups similar to those used in the cephalosporin, penicillin, and peptide arts can also be used to protect a carboxy group substituent of the compounds provided herein. Further examples of these groups are found in E. Haslam, "Protective Groups in Organic Chemistry", J. G. W. McOmie, Ed., Plenum Press, New York, N.Y., 1981, Chapter 5 and T. W. Greene, "Protective Groups in Organic Synthesis", 2nd Ed., John Wiley and Sons, New York, N.Y., 1991, Chapter 5.

The term "α center amino acid protecting group" as used herein refers to a subset of amino protecting groups that are used to protect the amino group in addition to a hydrogen alpha to the amino group from base promoted racemization. Examples of such groups include the trityl group [Cherney, R. J. and Wang, L., *J. Org. Chem.* 61:2544 (1996); Christie, B. D.; Rapoport, H., *J. Org. Chem.* 50:1239 (1985)] and the phenylfluorenyl group [Guthrie, R. D. and Nicolas, E. C., *J. Am. Chem. Soc.* 103:4638 (1981)].

The term "hydroxy activation agent" refers to organic or inorganic acids, acid halides, and acid anhydrides that are capable of converting a hydroxyl group into a leaving group labile to base treatment or nucleophilic displacement. Typical hydroxy activation agents include, but are not limited to sulfonating agents such as, methane sulfonyl chloride, p-toluenesulfonyl chloride, phenylsulfonyl chloride, trifluoromethylsulfonyl chloride, and the like, acylating agents such as isobutyl chloroformate, acetyl chloride, and the like, and halogenating reagents such as thionyl chloride, phosphorus tribromide, and the like.

The term "activated hydroxy group" refers to the moiety that results when a compound containing a hydroxy group is reacted with a hydroxy activating reagent e.g. the transformation from O—H to O-methylsulfonyl, O-p-toluenesulfonyl, O-phenylsulfonyl, O-trifluoromethylsulfonyl, O-isobutylacetyl, O-acetyl, chloro, or bromo.

"Pharmaceutically-acceptable salt" refers to salts of the compounds of the Formula I which are substantially non-toxic to mammals. Typical pharmaceutically-acceptable salts include those salts prepared by reaction of the compounds of the present invention with a mineral or organic acid or an organic or inorganic base. Such salts are known as acid addition and base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

Acids commonly employed to form acid addition salts are inorganic acids such as, without limitation, hydrochloric acid, hydrobromic acid, hydriodic acid, sulfuric acid, phosphoric acid, and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxides, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Examples of such pharmaceutically-acceptable salts are, without limitation, the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6 -dioate, benzoate, chlorobenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like salts of the compound of Formula I. The preferred acid addition salts are those formed with mineral acids, such as, without limitation, hydrochloric acid, and hydrobromic acid, and those formed with organic acids, such as, without limitation, maleic acid and methanesulfonic acid. The potassium and sodium salt forms are particularly preferred base addition salts.

"Pharmaceutically-effective amount" means that amount of a compound that will elicit the biological or medical response of a tissue, system, or mammal that is being sought by a researcher or clinician.

The geometric property that is responsible for the non-identity of an object with its mirror image is called chirality. A compound that having a single chiral center may exist in either of two forms that are mirror images of each other. "Enantiomer" usually designates one of the two forms of such a compound. Enantiomer may also designate a homochiral collection molecules of a compound, or a heterochiral collection of molecules of a compound that contains an excess of one enantiomer over the other enantiomer. Absolute structural configuration of enantiomers of a chiral compound is designated by the letters "R" or "S", using the rules of R. S. Cahn, C. K. Ingold, and V. Prelog in *Agnew. Chem.*, 78:413 (1966); *Agnew. Chem. Int. Ed.*, 5:385 (1966). An equimolar mixture of two enantiomers whose physical state is unspecified is called a "racemate". The adjectival form is "racemic", as in "racemic substance." The term "racemate" includes within it "crystalline racemate", which may refer to a conglomerate, a racemic mixture, a racemic compound, or a pseudoracemate [J. Jacques, A. Collet, and S. H. Wilen, *Enantiomers, Racemates, and Resolutions,* Krieger Publ. Co., Malabar, Fla., 1991, pp. 4–5]. The asymmetric carbon atom at the position denoted by the star (*) creates the chirality of the compounds of Formula (I).

(I)

It will be understood that preferred groups listed immediately below can be combined to create further, more narrowly limited groups of compounds. Preferred compounds are those wherein:

Q is —(CH$_2$)$_p$—;
Q is —(CH$_2$)—;
Q is —(CH$_2$)$_2$—;
Q is —(CH$_2$)$_3$—;
p is 1;
p is 2 or 3;
Q is —CH$_2$—O—CH$_2$—;
R$^0$ is selected from the group consisting of R$^0$ is R$^0$ is R$^0$ is R$^2$ is arylcarbonyl, aryloxycarbonyl, arylaminocarbonyl, aryl C$_{1-4}$ alkyloxycarbonyl, aryloxy C$_{1-4}$ alkylcarbonyl, or aryl C$_{1-4}$ alkylsulfonyl;
R$^2$ is arylcarbonyl, aryloxycarbonyl, aryl C$_{1-4}$ alkyloxycarbonyl, aryloxy C$_{1-4}$ alkylcarbonyl, or aryl C$_{1-4}$ alkylsulfonyl;
R$^2$ is arylcarbonyl, aryloxycarbonyl, or aryl C$_{1-4}$ alkyloxycarbonyl;
R$^2$ is arylcarbonyl;
R$^2$ is aryloxycarbonyl R$^2$ is arylaminocarbonyl;
R$^2$ is aryl C$_{1-4}$ alkyloxycarbonyl;
R$^2$ is aryloxy C$_{1-4}$ alkylcarbonyl;
R$^2$ is aryl C$_{1-4}$ alkylsulfonyl;
R$^2$ is benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, or phenyloxymethylcarbonyl, benzylaminocarbonyl;
R$^3$ is hydrogen;
R$^3$ is methyl;
R$^3$ is ethyl;
R$^3$ is n-propyl or iso-propyl;
R$^3$ is n-butyl, sec-butyl, or tert-butyl;
R$^4$ is hydrogen;
R$^4$ is methyl;
R$^5$ is —COOH;
R$^5$ is —CONR$^{10}$R$^{11}$;

R$^5$ is

R$^6$ is aryl;

It likewise will be understood that the particularly preferred groups listed immediately below can be combined to create further, more narrowly limited groups of compounds. Particularly preferred compounds are those wherein:

Q is —(CH$_2$)$_p$—;
Q is —(CH$_2$)—;
p is 1;
Q is —CH$_2$—O—CH$_2$—;

R$^0$ is

R$^2$ is arylcarbonyl;
R$^2$ is aryloxycarbonyl
R$^2$ is aryl C$_{1-4}$ alkyloxycarbonyl;
R$^2$ is benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, or phenyloxymethylcarbonyl, benzylaminocarbonyl;
R$^3$ is hydrogen;
R$^5$ is —COOH;
R$^6$ is aryl;
R$^6$ is phenyl;
R$^7$ is hydrogen;
W is —(CH$_2$)$_2$—;
Y is attached at position 3;

Y is attached at position 4;
Y is —O—;
Y is —S—;
n is 2
the compound is the R enantiomer;
the compound is the S enantiomer.
$R^6$ is aryl $C_{1-4}$ alkyl;
$R^6$ is aryl methyl;
$R^6$ is phenyl;
$R^6$ is benzyl;
$R^7$ is hydrogen;
$R^7$ is halogen;
$R^7$ is $C_{1-4}$ alkyl;
$R^7$ is fluorine;
$R^7$ is methyl;
$R^9$ is hydrogen;
$R^9$ is $C_{1-4}$ alkyl;
$R^9$ is methyl;
$R^{10}$ and $R^{11}$ are independently hydrogen or $C_{1-4}$ alkyl;
$R^{10}$ and $R^{11}$ are independently hydrogen;
$R^{10}$ and $R^{11}$ are independently $C_{1-4}$ alkyl;
W is —(CH$_2$)—;
W is —(CH$_2$)$_2$—;
W is —(CH$_2$)$_3$—;
W is —(CH$_2$)$_4$—;
Y is attached at position 3;
Y is attached at position 4;
Y is —O—;
Y is —S—, —SO—, or —SO$_2$—;
Y is —S—;
Y is —CONR$^9$—, —NR$^9$—SO$_2$—, or —SO$_2$—NR$^9$—;
Y is —SO$_2$—, —NR$^9$—SO$_2$—, or —SO$_2$—NR$^9$—;
n is 1;
n is 2;
n is 3;
n is 4;
the compound is the R enantiomer;
the compound is the S enantiomer;
the compound is the racemate;
Further preferred compounds of Formula (I) are those wherein:

$R^0$ is 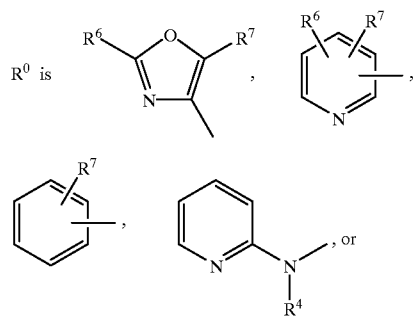

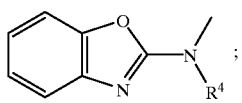

$R^2$ is arylcarbonyl, aryloxycarbonyl, arylaminocarbonyl, aryl $C_{1-4}$ alkyloxycarbonyl, aryloxy $C_{1-4}$ alkylcarbonyl, or aryl $C_{1-4}$ alkylsulfonyl;
$R^3$ is hydrogen or methyl;
$R^4$ is hydrogen or methyl;
$R^5$ is —COOH, —CONR$^{10}$R$^{11}$, or

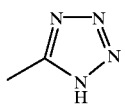

$R^6$ is aryl;
$R^7$ is hydrogen, halogen, or methyl;
$R^{10}$ and $R^{11}$ are hydrogen;
Y is —O— or —S—;
the compound is the R enantiomer;
the compound is the S enantiomer; and
the compound is the racemate.
More preferred compounds of Formula I are those wherein:

$R^0$ is 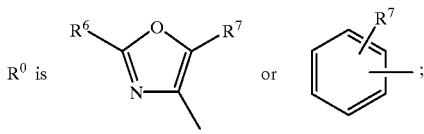

$R^2$ is arylcarbonyl, aryloxycarbonyl, aryl $C_{1-4}$ alkyloxycarbonyl, or aryl $C_{1-4}$ alkylsulfonyl;
$R^5$ is —COOH;
$R^7$ is hydrogen, fluoro, or methyl;
Y is —O—; and
n is 1 or 2.
Particularly preferred compounds of Formula I are those wherein:
Q is —(CH$_2$)— or —(CH$_2$)—O—(CH$_2$)—;

$R^0$ is 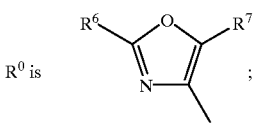

$R^2$ is benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, or phenyloxymethylcarbonyl, benzylaminocarbonyl;
$R^6$ is phenyl;
$R^7$ is hydrogen;
Y is attached at the 3 position;

Y is attached at the 4 position; and n is 2.

Preferred aryl radicals include phenyl, 1-naphthyl, and 2-naphthyl, optionally substituted with $C_{1-4}$ alkyl, $C_{1-4}$ alkoxy, halogen, —$NO_2$, or triflurormethyl. A more preferred aryl radical is phenyl, optionally substituted with $C_{1-4}$ alkyl, $C_{1-4}$ alkoxy, halogen, —$NO_2$, or triflurormethyl. A particularly preferred aryl radical is phenyl, optionally substituted at the para-position with methyl, ethyl, n-propyl, n-butyl, methoxy, fluoro, chloro, bromo, or trifluoromethyl.

A few compounds of this invention will be specifically mentioned to assure the reader's comprehension. This invention includes both racemates, and individual enantiomers.

4-(2-naphthylmethylsulfonyl)benzyl-N-ethoxycarbonyl-serine-carbonitrile;

O-(2-(2-(2-naphthyl)-5-fluoro-4-thiazolyl)propyl)-N-benzoxycabonyl-tyrosine, free acid;

O-(3-(2-(2-flurorphenyl)ethylsulfinyl)benzyl)-N-benzoxycabonyl-serine, free acid;

O-(2-(methyl-2-pyridylamino)ethyl)-N-benzoxycabonyl-tyrosine, free acid;

O-(2-(2-benzoxazolylmethylamino)ethyl)-N-benzoxycabonyl-tyrosine, calcium salt;

O-(4-(4-(methyl-2-pyridylamino) butylaminosulfonyl) benzyl)-N-benzoxycabonyl-serine, free acid;

O-(4-(3-(2-benzoxazolylmethylamino) propylcarbonylamino)benzyl)-N-benzoxycabonyl-serine, lithium salt;

O-[2-(2-phenyl-5-methyl-4-oxazolyl)ethyl]-N-benzyloxycarbonyl-tyrosine, free acid;

O-[2-(2-phenyl-4-oxazolyl)ethyl]-N-benzyloxycarbonyl-tyrosine, sodium salt;

α-(3-[2-(4-(2-naphthyl)phenyl)ethylamino]benzyl)-N-benzyloxycarbonyl-glycine, potassium salt;

O-(4-[4-(2-(2-furyl)-5-methyl-4-thiazolyl)butylsulfoxyl] benzyl)-N-benzyloxycarbonyl-serine, free acid;

O-(3-[2-(6-(2-pyridyl)-2-naphthyl)ethylaminosulfonyl] benzyl])-N-benzyloxycarbonyl-serine, calcium acid; and O-[4-(3-phenyl-2-pyridylamino)butyl]-N-benzylcarbonyl-tyrosine, lithium salt.

A series of Schemes is presented below to familiarize the reader with chemical reactions and intermediates in the synthesis of compounds of Formula I. All substituents previously defined have the same meanings in the Schemes below. The substituent "R" in the Schemes below represents a carboxyl-protecting group. The substituent "X" in the Schemes below represents leaving group, such as a halogen.

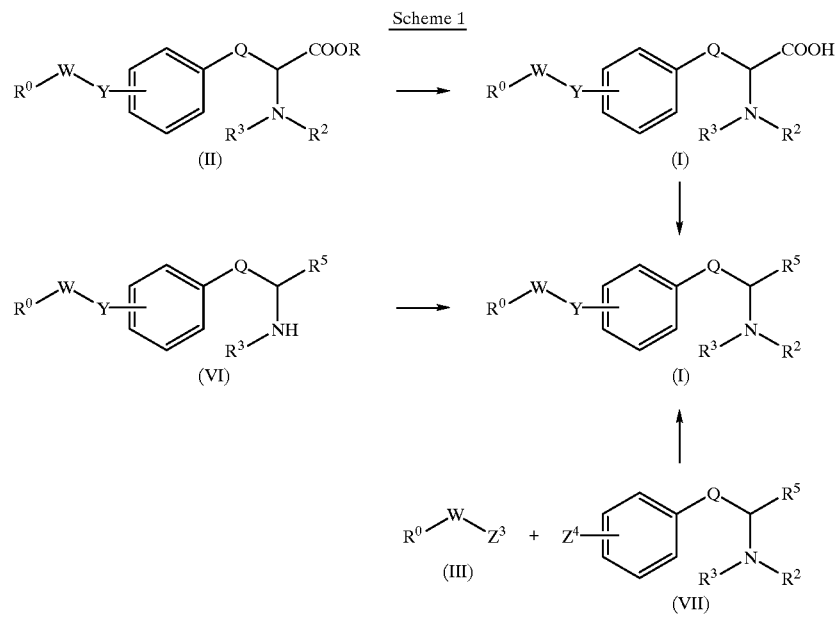

Scheme 1

As described below in Schemes 2–4, compounds of Formula (I) wherein $R^5$ is —COOH may be formed from compounds of Formula II by deprotecting the carboxyl group, following methods described in Greene and Wuts, Chapter 5, and then, optionally, forming another of the substituents of $R^5$. Compounds of Formula I wherein $R^2$ is other than hydrogen may be formed from compounds of Formula VI by adding the desired $R^2$ substituent at the nitrogen atom of the compound of Formula VI as described in Greene and Wuts, Chapter 7, or in Schemes 13 and 14 herein. Compounds of Formula I may also be formed by reacting a compound of Formula III with a compound of Formula VII, as elaborated in Schemes 5–9 herein.

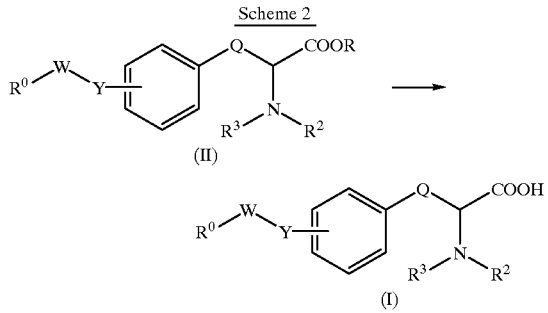

Compounds of Formula I wherein $R^5$ is —COOH may be derived from compounds of Formula II by deprotecting the 3-carboxylic acid group using methods described in Greene and Wuts, Chapter 5.

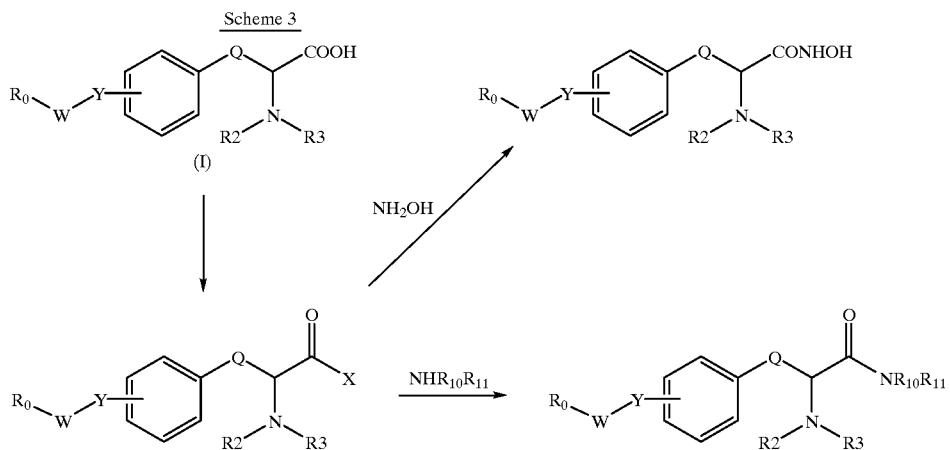

Optionally, a compound of Formula I wherein $R^5$ is —CONH$_2$, —CN, —CONHOH, or

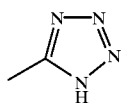

may be formed from compounds of Formula I wherein $R^5$ is —COOH, or an ester of —COOH. A first step is to form the acyl halide of (I) by reacting (I) wherein $R^5$ is —COOH with thionyl chloride, phosphorus pentachloride, or phosphorus tribromide. Reaction of the acyl halide of (I) with hydroxylamine yields (I) wherein $R^5$ is —CONHOH (the hydroxamate) (March, *Advanced Organic Chemistry*, McGraw-Hill, New York, 1968, page 335). Alternatively, where the —COOH is esterified, the ester may be treated with hydroxylamine hydrochloride and base, such as, potassium carbonate. Reaction of the acyl halide of (I) with ammonia, a primary amine, or secondary amine yields (I) wherein $R^5$ is —CONR$^9$R$^{10}$. (Sonntag, *Chem. Rev.* 52:258–294, 1953).

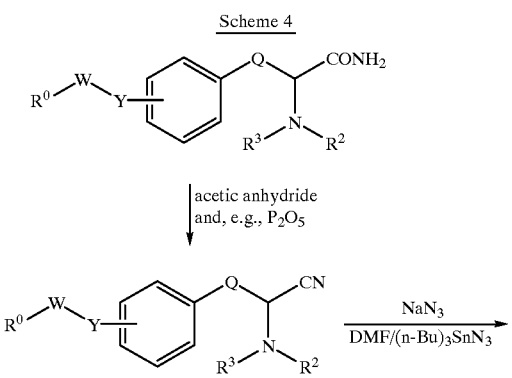

-continued

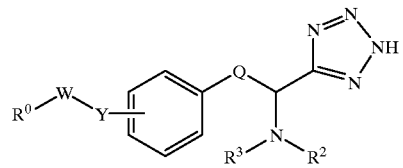

Treatment of a compound of Formula I wherein $R^5$ is —CONH$_2$ with an efficient dehydrating agent, such as P$_2$O$_5$, POCl$_3$, or SOCl$_3$, and acetic anhydride will convert it to a compound of formula (I) wherein $R^5$ is —CN (Ugi, et al., *Angew. Chem. Intern. Ed. Engl.* 4:472–484, 1965; also, March, pages 777–778). A compound of Formula I wherein $R^5$ is

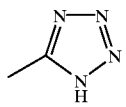

is made from a compound of Formula I wherein $R^5$ is —CN by reacting it with sodium azide in a solvent such as dimethylformamide at about 140 degrees Centigrade together with a tin reagent, such as tri-n-butyl tin azide (*Encyclopedia of Reagents for Organic Synthesis*, ed. by L. A. Paquette, J. H. Wiley & Sons, New York, 1995, vol. 7, pp. 5035–5037).

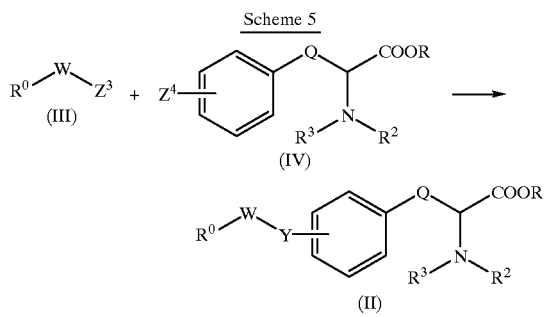

Scheme 5

Compounds of Formula II may be made by addition of a compound of Formula III to a compound of Formula IV. Substituent $Z^3$ of (III) and substituent $Z^4$ of (IV) are such that reaction of (III) and (IV) results in the formation of Y. Depending on the type of Y group sought, $Z^3$ may be —OH, —SO$_2$Cl, —X (halogen), —NHR$^9$, or —COCl and $Z^4$ may be —OH, —SH, —NH$_2$, or —SO$_2$Cl, for example. Scheme 5 shows the general reaction. Schemes 6–9 show the formation of specific Y groups. The table below shows the substituents $Z^3$ and $Z^4$ that might be selected for each group, Y. The particular selections of $Z^3$ and $Z^4$ are not meant to limit the groups that the skilled chemist might use to form Y of the compounds of Formula I.

| Y | $Z^3$ | $Z^4$ |
|---|---|---|
| —O— | —OH | HO— |
| —S— | —X | HS— |
| —SO— | —X | HS— |

-continued

| Y | $Z^3$ | $Z^4$ |
|---|---|---|
| —SO$_2$— | —X | HS— |
| —NH— | —X | $_2$HN— |
| —CONR$^9$— | —COX | HR$^9$N— |
| —SO$_2$NR$^9$— | —SO$_2$Cl | $_2$HN— |
| —NR$^9$SO$_2$— | —NH$_2$ | ClO$_2$S— |

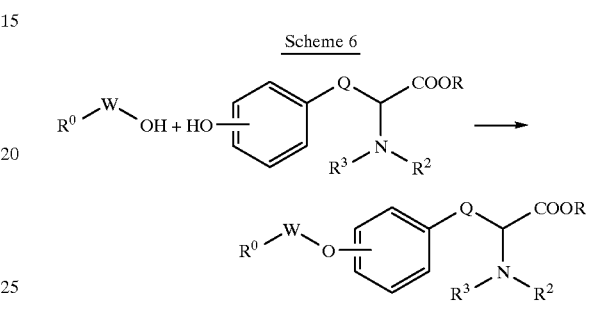

Scheme 6

Where $Z^3$ is —OH, and $Z^4$ is —OH, compounds of Formula II wherein Y is —O— are synthesized by a standard method, such as the Mitsunobu reaction (*Synthesis*, p. 1, 1981; Hughes, D. L., *Organic Reactions* 42:336, 1992; Bose, A. K., et al., *J. Can. Chem.* 62:2498, 1984), as further exemplified in Example 1.

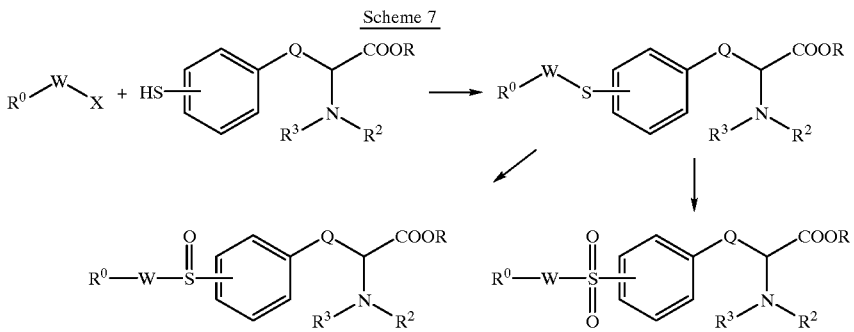

Scheme 7

To obtain a thioether, wherein Y of (II) is —S—, $Z^3$ of (III) is —X (a halogen) and $Z^4$ of (IV) is —SH (March, page 1171). The compound of Formula II wherein Y is —SO— may be formed from the thioether by oxidation using one equivalent of hydrogen peroxide (March, page 887). The compound of Formula II wherein Y is —SO$_2$— may be formed from the thioether by further oxidation using two equivalents of hydrogen peroxide, or using potassium permanganate, or other oxidizing agents (March, page 887).

Scheme 8

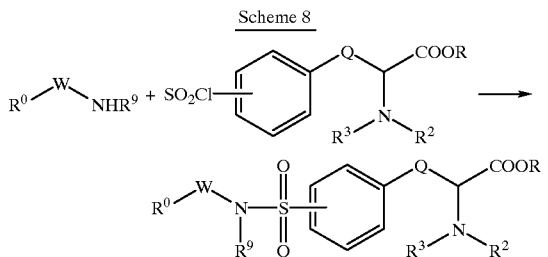

A compound of Formula (II) wherein Y is —NR$^9$SO$_2$— is formed by reaction of compound III wherein Z$^3$ is —NHR$^9$, and compound IV wherein Z$^4$ is —SO$_2$Cl (March, page 374).

Scheme 10

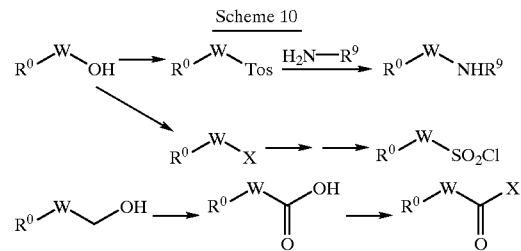

Compounds of Formula III are synthesized using known reactions (A. R. Katritsky, *Handbook of Heterocyclic Chemistry*, Pergamon Press, 1985). Compounds of Formula III wherein Z$^3$ is —NHR$^9$, —SO$_2$Cl, or —X may be made Scheme 9

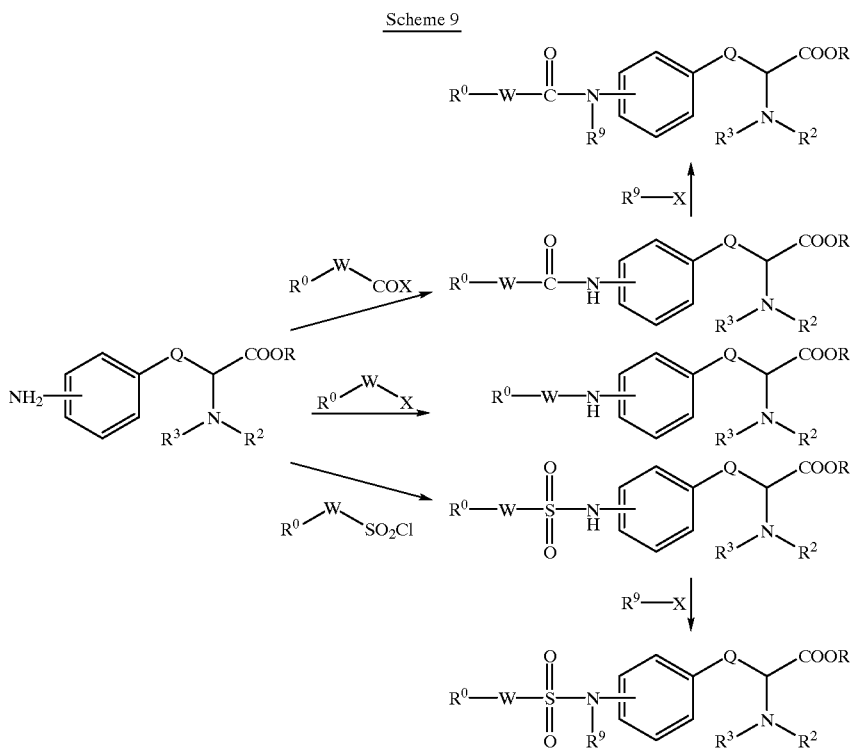

Where Z$^3$ is —COX and Z$^4$ is —NH$_2$, compound (II) wherein Y is —CONH—, is formed by amidation of an acid chloride (March, page 335). Reaction of (III) wherein Z$^3$ is —X with (IV) wherein Z$^4$ is —NH$_2$, under conditions favorable for alkylation of the amine as described by March, page 331, results in the synthesis of (II) wherein Y is —NH—. A compound of Formula II wherein Y is —SO$_2$NH— is formed by reaction between a compound of Formula III wherein Z$^3$ is —SO$_2$Cl and a compound of Formula IV wherein Z$^4$ is —NHR$^9$ (March, page 374). A compound of Formula II wherein Y is —SO$_2$NR$^9$— or —CONR$^9$— may be subsequently formed using an alkyl halide (R$^9$-X) (March, page 340).

from a compound of Formula III wherein Z$^3$ is —OH (the alcohol). Where Z$^3$ is —NHR$^9$, the alcohol is converted to an amine, for example, by formation of a tosylate or mesylate followed by nucleophilic displacement with a substituted or unsubstituted amine (I. T. Harrison and S. Harrison, *Compendium of Organic Synthetic Methods*, Wiley-Interscience, New York, 1971, pp. 232, and 250–255). Where Z$^3$ is —SO$_2$Cl, the alcohol may be converted to a halide (March, p. 343), which on subsequent treatment with sodium bisulfite is converted to a sulfonic acid sodium salt (S. R. Sandler and W. Karo, *Organic Functional Group Preparations*, Academic Press, New York, 1968, p. 512). Treatment of the sulfonic acid sodium salt with chlorosul fonic acid, for example, then produces the sulfonyl chloride (Sandler and Karo, p, 517). Where $Z^3$ is —X, the alcohol is treated with a halogen acid, or an inorganic acid halide (March, page 343). To make a compound of Formula III wherein $Z^3$ is —COX, a compound of formula

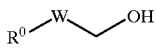

may be oxidized to an acid (Harrison and Harrison, pp. 26–30), from which the halide may be formed (Harrison and Harrison, pp. 18–22).

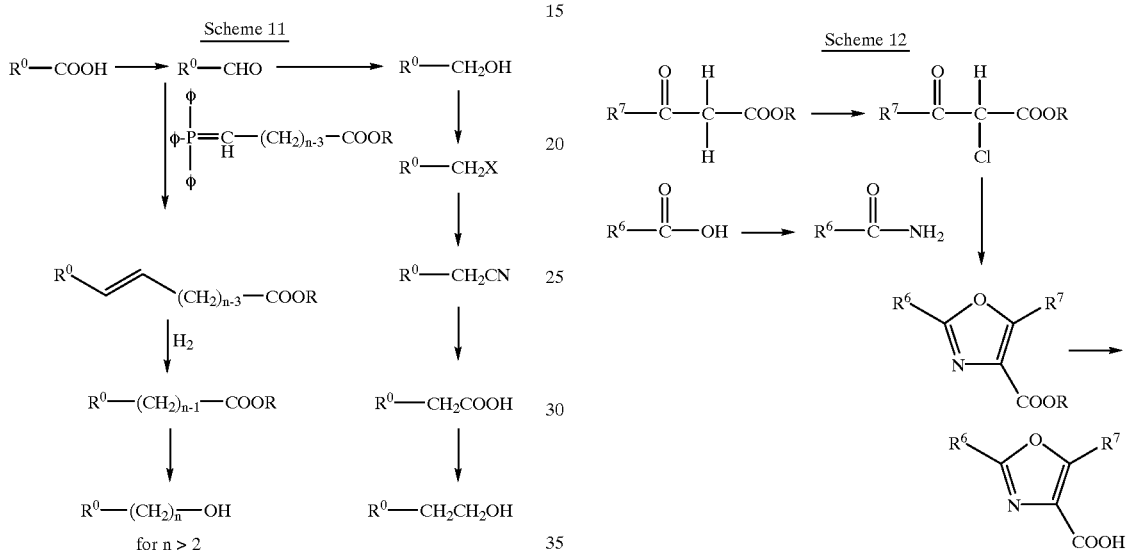

Scheme 11 shows syntheses of various alcohols used as starting material in Scheme 10. Partial reduction of the acid, $R^0$-COOH, to the aldehyde (Harrison and Harrison, pp. 132–137) followed by Wittig condensation (March, pp. 845–854), olefin reduction (Harrison and Harrison, pp. 198–202) and further reduction to the alcohol (Harrison and Harrison, pp. 76–78), with or without saponification, will produce $R^0$-$(CH_2)_n$-OH, for n greater than 2. Full reduction of the acid $R^0$-COOH, will produce $R^0$-$CH_2$-OH. The alcohol $R^0$-$CH_2$-OH may be homologated to $R^0$-$(CH_2)_2$-OH by standard methods, such as, conversion to halide (March, p. 343), displacement with cyanide (Harrison and Harrison, pp. 468–470), hydrolysis of the resulting nitrile to a carboxylic acid (Harrison and Harrison, pp. 62–64), and reduction of the acid to the alcohol (Harrison and Harrison, pp. 76–78).

Where $R^0$ is

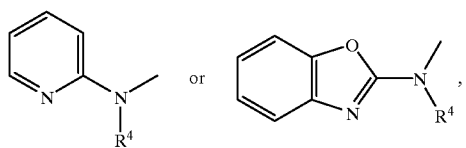

the intermediate of the form $R^0$-$(CH_2)_n$-OH may be synthesized following Cantello, et al., *J. Med. Chem.*, 37:3977–3985, 1994.

Where $R^0$ is

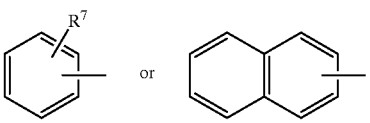

the reactions of Scheme 11 are followed starting with readily-available carboxylic acid, aldehyde, or alcohol derivatives of $R^0$.

Scheme 12 demonstrates a method to form intermediate compounds of the form $R^0$-COOH which are used in Scheme 11. Where $R^0$ is oxazole the method of L. A. Paquette, *Principles of Modern Heterocyclic Chemistry*, W. A. Benjamin, 1968, page 191, may be followed. A substituted thiazole may be obtained using the same scheme, but substituting the corresponding thioamide, following Paquette, page 193. The pyridyl intermediate of form $R^0$-COOH may be prepared by the method of E. H. Rood, ed., Chemistry of Carbon Compounds, Vol. IV[A], Elsevier Publ. Co., 1957, page 557.

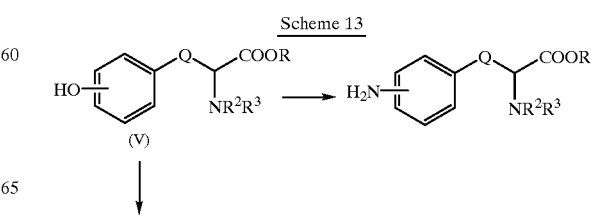

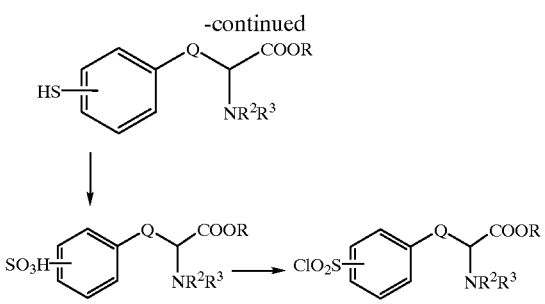

A compound of Formula IV, wherein $Z^4$ is —OH may be formed according to Scheme 15, below. The aromatic hydroxy group may be optionally transformed by known reactions to form other compounds of Formula IV, wherein $Z^4$ is —SH, —NH$_3$, or —SOCl$_2$. For example, the amine derivative is formed using 4-chloro-2-phenylquinazoline (Fieser and Fieser, 4, 86). The compound of Formula IV wherein $Z^4$ is —SH may be formed by treating a compound of Formula IV wherein $Z^4$ is —OH with dimethylthiocarbamyl halide in the presence of hydroxide ion at elevated temperature using Newman's method (Fieser and Fieser 4, 202). A compound of Formula IV wherein $Z^4$ is —SO$_3$ is formed from a compound of Formula IV wherein $Z^4$ is —SH by oxidation.

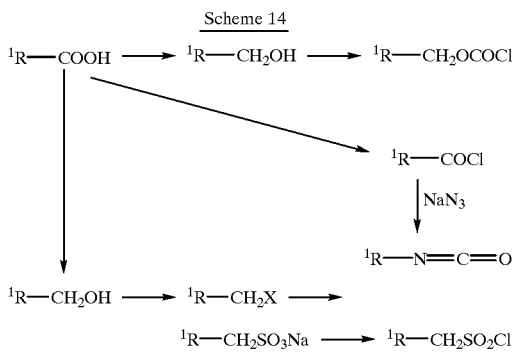

Reagents for attaching the substituent $R^2$ may be prepared as shown in Scheme 14, or may be found in Greene and Wuts, Chapter 7. For example, where it is desired that $R^2$ be a an aryl $C_{1-4}$ alkyloxycarbonyl group, the synthesis of Scheme 14 could start with the corresponding aryl $C_{0-3}$ alkyl acid. The acid could be reduced to the alcohol, and the alcohol reacted with phosgene and base, for example, to yield the corresponding oxycarbonyl chloride. Alternatively, the corresponding alcohol could serve as the starting point if it were available.

An acyl halide or an aryl acyl halide may be used to form the compound of Formula I wherein $R_2$ is aryl $C_{1-4}$ acyl. The acyl halide is formed from the acid by standard methods, such as reaction of the acid with thionyl chloride, phosphorus pentachloride, or phosphorus tribromide.

An isocyanate derivative may be used to form the compound of Formula I wherein $R_2$ is $C_{1-4}$ alkylaminocarbonyl, arylaminocarbonyl, or aryl $C_{1-4}$ alkylaminocarbonyl. The isocyanate may be formed from the acid halide by reaction with sodium azide (Fieser and Fieser, 1, 1041).

A sulfonyl chloride reagent may be used to create the compound of Formula I wherein $R^2$ is aryl $C_{1-4}$ alkylsulfonyl. The sulfonyl chloride reagent may be formed from an acid by reducing the acid to an alcohol, and then following the sequence described in Scheme 14.

In Scheme 14, $R^1$ is a group such that reaction between a compound at the right side of Scheme 13 and the nitrogen atom to which the group $R^2$ is to be attached leaves a group defined as $R^2$ attached to said nitrogen atom. The relation between the groups $R^1$, $R^2$, and the compound used to derivatize the nitrogen atom are shown for some representative groups in the table below.

| $R_2$ | $R^1$ | Compound to Derivatize Nitrogen Atom |
|---|---|---|
| benzyloxycarbonyl | phenyl | $R^1$—CH$_2$—O—COCl |
| phenylcarbonyl | phenyl | $R^1$—COCl |
| benzylcarbonyl | benzyl | $R^1$—COCl |
| ethyloxycarbonyl | ethyl | $R^1$—O—COCl |
| n-butylaminocarbonyl | n-butyl | $R^1$—N=C=O |
| phenylmethylsulfonyl | phenyl | $R^1$—CH$_2$—SO$_2$Cl |

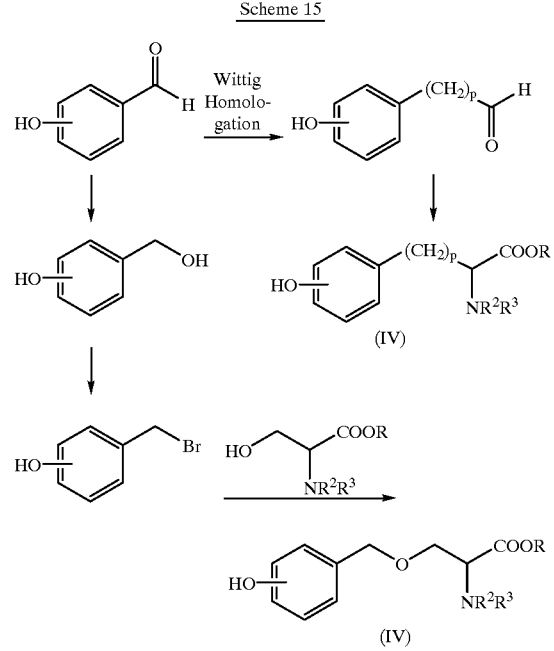

The compound of Formula (IV), used as starting material in Scheme 13, wherein Q is —(CH$_2$)$_p$— may be synthesized from 3- or 4-hydroxybenaldehyde using Wittig homologation (J. Chem. Soc. Perkin, 1:3099, 1979) either once, or successively, depending on the value of p, and then forming the amino acid with protected carboxylic acid and amino groups from the resulting aldehyde as described in Organic Synthesis Coll., 1:21.

The compound of Formula (IV) wherein Q is —CH$_2$—O—CH$_2$— is made from 3- or 4-hydroxybenzaldehyde by reducing the aldehyde, forming 3- or 4-hydroxybenzylbromide from the alcohol, reacting the bromide with serine having its carboxyl and amino groups protected, and finally, removing the protecting groups.

Compounds of formula (IV) wherein Q is —CH$_2$-O-CH$_2$— and Y is —O— may also be prepared as illustrated in Scheme 16 below where H.A.A. is a hydroxy activating agent, $R^8$ is an activated hydroxy group, Pg is an α center amino acid protecting group, and R is a carboxy protecting group.

Scheme 16

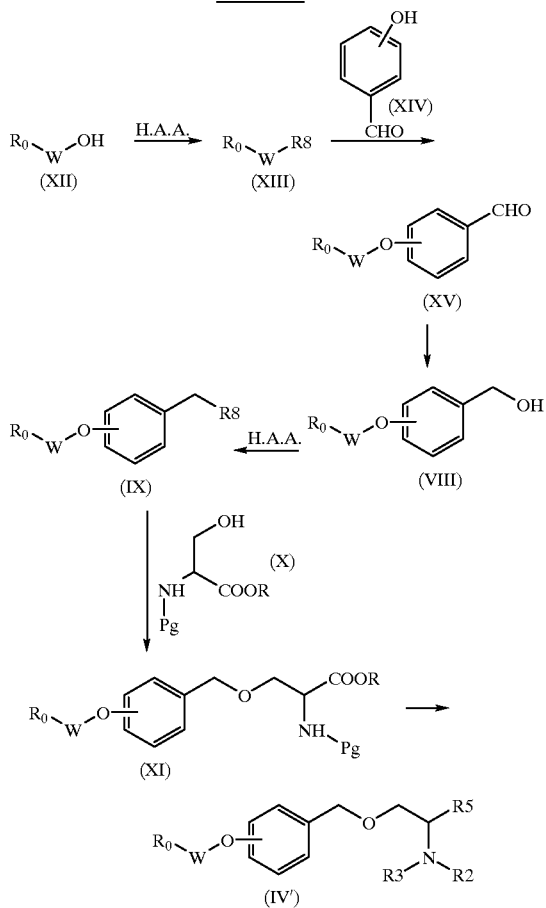

For example, a hydroxy activating agent (H.A.A.) may be added to a compound of formula (XII), dissolved or suspended in a suitable organic solvent, to form a compound of (XIII), wherein $R^8$ is an activated hydroxy group. Suitable organic solvents include, but are not limited to, chloroform, 1,2-dichloroethane, diethyl ether, acetonitrile, ethyl acetate, 1,3-dimethyl-2-imidazolidinone, tetrahydrofuran, dimethylformamide, toluene, chlorobenzene, dimethylsulfoxide, mixtures thereof, and the like. Methylene chloride is typically the preferred solvent. The choice of hydroxy activating agents is not critical but methanesulfonyl chloride is preferred. When a sulfonating or acylating hydroxy activating reagent is used, the reaction is preferably run in the presence of a suitable base. Suitable bases include, but are not limited to, carbonates, bicarbonates, and hydroxides (e.g. lithium, sodium, or potassium carbonate, bicarbonate, or hydroxide), or trialkylamines. The preferred base is triethylamine. The hydroxy activating agent is typically employed in a molar excess. For example, a 1.1 to a 1.5 molar excess relative to the compound of formula I is usually employed. A 1.25 molar excess is typically preferred. The base is also typically employed in a molar excess. For example, a 1.2 to a 1.6 molar excess relative to the compound of formula I is generally employed. A 1.4 molar excess is typically preferred. The reaction is generally performed at a temperature from −50° C. to ambient temperature but is preferably performed at about 5° C. for from about 1 to 3 hours.

Compounds of formula (XIII) may then be reacted with commercially-available 4-hydroxybenzaldehyde or 3-hydroxybenzaldehyde, compounds of formula (XIV), in a suitable organic solvent in the presence of a suitable base, to form a substituted hydroxybenzaldehyde, a compound of formula (XV), as shown in Scheme 16. Suitable organic solvents include those mentioned as suitable organic solvents above, but dimethylformamide is preferred. Suitable bases include those mentioned as suitable bases above, but cesium carbonate is preferred. The compound of formula (XIII) and the base are typically employed in a slight molar excess. For example, a 1.01 to a 1.25 molar excess relative to the hydroxybenzaldehyde compound, (XIV), is usually employed. A 1.1 molar excess is typically preferred. The reaction is generally performed at a temperature from ambient to about the reflux temperature of the solvent but is preferably performed at about 45° C. for from about 5 to 12 hours.

The aldehyde moiety of compound of formula (XV) may be reduced to an alcohol moiety, as shown in Scheme 16. Methods for reducing aldehydes to their corresponding alcohols are found in Larock, *Comprehensive Organic Transformations*, VCH Publishers, Inc., New York, N.Y., 1989, pg. 527. Specifically, the substituted hydroxybenzaldehyde, dissolved or suspended in a suitable organic solvent, is treated with a reducing agent, to form a compound of formula (VIII). Suitable organic solvents include those mentioned as suitable organic solvents above, in addition to lower alcohols. Isopropanol is usually a convenient and preferred solvent. Sodium borohydride is typically a convenient and preferred reducing agent. The reducing agent is typically employed in a molar excess but the magnitude of the excess will vary with the reducing agent employed. For example, when sodium borohydride is the reducing agent a 1.5 to a 3 molar excess, relative to the compound of formula (XV) is generally employed. A 2 molar excess is typically preferred. The reaction is typically and preferably performed at ambient temperature for about 18 hours.

A compound of formula (IX) may be prepared from a compound of formula (VIII) by activating the hydroxy group in the same manner as described above. The preferred solvent is methylene chloride and the preferred hydroxy activating reagent is phosphorous tribromide. The skilled artisan will recognize that when a halogenating reagent is the hydroxy activating agent, the presence of a base may be required, depending on the agent used. The reaction is preferably run at about 5° C. when adding the halogenating reagent and then at ambient temperature for about 2 hours.

Compounds of formula (XI) may be prepared from compounds of formula (IX) and a commercially-available amino and carboxy protected serine of formula (X). For example, a solution of a compound of formula (IX) in an organic solvent may be added to an alkaline aqueous solution of a compound of formula (X) in the presence of a phase transfer catalyst. Suitable organic solvents include chloroform, 1,2- dichloroethane, ethyl acetate, toluene, chlorobenzene, mixtures thereof, and the like. Methylene chloride is typically the preferred organic solvent. The choice is bases which make the aqueous phase alkaline is not critical but sodium hydroxide is preferred. The compound of formula (IX) is typically employed in a slight molar excess. For example, a 1.05 to a 1.25 molar excess relative to the compound of formula (X) is usually employed. a 1.1 molar excess is typically preferred. Choice of phase transfer catalysts is not critical but tetrabutylammonium bromide is preferred. The reaction is generally performed at a temperature from ambient to the reflux temperature of the solvent and is preferably performed at about 40° C. for from about 12 to 36 hours, typically 24 hours. For further illustration see e.g. Palmer, M.J., et al, *Synlett*, 1994, 171. For alternate methods for producing compounds of formula (XI) from compounds of formula (IX) and (X) see e.g. Cherney, R.J.; Wang, L., *J. Org. Chem.* 61, 2544 (1996).

Methods for removing trityl or phenylfluorenyl amino protecting groups in compound (XI) may be found in T. W. Greene, "Protective Groups in Organic Synthesis", John Wiley and Sons, New York N.Y., 1981, pgs. 366–367 and the Examples section which follows. Methods for removing carboxy protecting groups without affecting amino protecting groups may be found in the Greene reference at 224–276 or in the Examples section which follows. The conversion of free carboxyl groups to other substituents is described above in Scheme 3.

The compounds of the present invention can be administered in oral forms, such as, without limitation, tablets, capsules, pills, powders, granules, elixirs, tinctures, suspensions, syrups, and emulsions. They may also be administered in parenteral forms, such as, without limitation, intravenous (bolus or infusion), intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skill in that art.

The dosage regimen utilizing the compounds of the present invention is selected by one of ordinary skill in the medical or veterinary arts, in view of a variety of factors, including, without limitations, the species, age, weight, sex, and medical condition of the recipient, the severity of the condition to be treated, the route of administration, the level of metabolic and excretory function of the recipient, the dosage form employed, the particular compound and salt thereof employed, and the like.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Therefore, yet another embodiment of the present invention is a pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining (e.g., mixing) a therapeutically effective amount of the compounds of the invention together with one or more pharmaceutically-acceptable excipients therefor. In making the compositions of the present invention, the active ingredient may be admixed with a diluent, or enclosed within a carrier, which may be in the form of a capsule, sachet, paper, or other container. The carrier may serve as a diluent, which it may be solid, semi-solid, or liquid material which acts as a vehicle, or can be in the form of tablets, pills, powders, lozenges, elixirs, suspensions, emulsions, solutions, syrups, aerosols (as a solid or in a liquid medium), ointments, containing, for example, up to 10% by weight of the active compound, soft and hard gelatin capsules, suppositories, sterile injectable solutions and sterile packaged powders.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, agar, bentonite, xanthan gum, alginic acid, and the like; and, optionally, binding agents, for example, without limitation, gelatin, acacia, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powders, the carrier is a finely divided solid which is in admixture with the finely divided active ingredient. In tablets, the active ingredient is mixed with a carrier having the necessary binding properties in suitable proportions and compacted in the shape and size desired. The powders and tablets preferably contain from about 1 to about 99 weight percent of the active ingredient which is the novel composition of the instant invention. Suitable solid carriers are magnesium carbonate, magnesium stearate, talc, sugar, lactose, pectin, dextrin, starch, gelatin, tragacanth, methylcellulose, sodium carboxymethyl cellulose, low melting waxes, and cocoa butter.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Preferably, the pharmaceutical formulation is in unit dosage form. A "unit dosage form" is a physically discrete unit containing a unit dose, suitable for administration in human subjects or other mammals. A unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved. It may be appreciated that it may be necessary to make routine variations to the dosage depending on the age and condition of the recipient. The dosage will also depend on the route of administration.

The oral route is most preferred. Typical oral dosages of the present invention, when used for the indicated effects, will range from about 0.01 mg per kg body weight per day (mg/kg/day) to about 50 mg/kg/day, preferably from 0.1 mg/kg/day to 30 mg/kg/day, and most preferably from about 0.5 mg/kg/day to about 10 mg/kg/day. The compounds of the present invention may be administered in a single daily dose, or the total daily dose may be administered in divided doses, two, three, or more times per day. Where delivery is via transdermal forms, of course, administration is continuous.

Administration to a human is most preferred. The human to whom the compounds and formulations of the present invention are administered has a disease or condition in which control blood glucose levels are not adequately controlled without medical intervention, but wherein there is endogenous insulin present in the human's blood. Non-insulin dependent diabetes mellitus (NIDDM) is a chronic disease or condition characterized by the presence of insulin in the blood, even at levels above normal, but resistance or lack of sensitivity to insulin action at the tissues. The compounds and formulations of the present invention are also useful to treat acute or transient disorders in insulin sensitivity, such as sometimes occur following surgery, trauma, myocardial infarction, and the like. The compounds and formulations of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who will benefit from administration of the compounds and formulations of the present invention.

The following formulation examples are illustrative only and are not intended to limit the scope of the invention in any way.

FORMULATION 1

Hard gelatin capsules are prepared by mixing the following ingredients and filling the mixture, in 460 mg quantities, into hard gelatin capsules.

| Ingredient | Quantity (mg/capsule) |
|---|---|
| O-[2-(2-phenyl-4-oxazolyl)ethoxy]-N-benzyloxycarbonyl-tyrosine, free acid | 250 |
| Starch, dried | 200 |
| Magnesium stearate | 10 |
| Total | 460 |

FORMULATION 2

A tablet containing 250 mg of the compound of the present invention is prepared by blending the components listed below and then compressing 665 mg of the blend into a tablet.

| Ingredient | Quantity (mg/tablet) |
|---|---|
| O-[2-(2-phenyl-4-oxazolyl)ethoxy]-N-benzyloxycarbonyl-tyrosine, sodium salt | 250 |
| Cellulose, microcrystalline | 400 |
| Silicon Dioxide, fumed | 10 |
| Stearic Acid | 5 |
| Total | 665 |

FORMULATION 3

A tablet containing 60 mg of the compound of the present invention is prepared as follows:

| Ingredient | Quantity (mg/tablet) |
|---|---|
| O-[2-(2-phenyl-4-oxazolyl)ethoxy]-N-benzyloxycarbonyl-tyrosine, potassium salt | 60 |
| Starch | 45 |
| Cellulose, microcrystalline | 35 |
| Polyvinylpyrrolidone, 10%, aqueous | 4 |
| Sodium carboxymethyl starch | 4.5 |
| Magnesium stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxylmethyl starch, magnesium stearate, and talc, previously passed though a No. 60 mesh U.S. sieve, are then added to the granules which, after mixing, are compressed on a tablet machine to yield tablets each weighing 150 mg.

FORMULATION 4

Capsules containing 80 mg of the active compound of the present invention are made as follows:

| Ingredient | Quantity (mg/capsule) |
|---|---|
| α-(3-[6-(2-phenyl-4-thiazolyl)hexylsulfinyl]benzyl)-N-benzyloxycarbonyl-glycine-carbonitrile, hydrochloride; | 80 |
| Starch | 59 |
| Cellulose, microcrystalline | 59 |
| Magnesium stearate | 2 |
| Total | 200 |

The active ingredient, starch, cellulose, and magnesium stearate are blended, the blend is passed through a No. 45 mesh U.S. sieve, and then hard gelatin capsules are filled with 200 mg of the blend.

FORMULATION 5

Suppositories each containing 225 mg of active compound of the present invention are made as follows:

| Ingredient | Quantity (mg/suppository) |
| --- | --- |
| O-[2-(5-butyl-2-(2-naphthyl)-4-oxazolyl)ethoxy]-N-para-chlorobenzylcarbonyl-tyrosine | 225 |
| Saturated fatty acid glycerides | 2,000 |
| Total | 2,225 |

The active compound is passed through a No. 60 mesh U.S. sieve and suspended in the saturated fatty acid glycerides, previously melted using the minimum heat necessary. The mixture is then poured into a suppository mold of nominal 2 g capacity and allowed to cool.

FORMULATION 6

Suspensions each containing 50 mg of active compound of the present invention per 5 mL dose are made as follows:

| Ingredient | Quantity per dose |
| --- | --- |
| O-(4-[2-(5-methyl-2-(2-furyl)-4-oxazolyl)ethoxy]benzyl)-N-phenylmethylsulfonyl-serine | 50 mg |
| Sodium Carboxymethyl Cellulose | 50 mg |
| Syrup | 1.25 mL |
| Benzoic Acid Solution | 0.10 mL |
| Flavor | q.v. |
| Color | q.v. |
| Purified Water to total volume: | 5 mL |

The active ingredient, starch, cellulose, and magnesium stearate are blended, the blend is passed through a No. 45 mesh U.S. sieve, and then hard gelatin capsules are filled with 200 mg of the blend.

FORMULATION 7

An intravenous formulation may be prepared as follows:

| Ingredient | Quantity |
| --- | --- |
| α-(3-[2-(2-(2,5-dimethylphenyl)-4-pyridyl)ethoxy]benzyl)-N-phenylmethylsulfonyl-glycine-tetrazole, sodium salt | 100 mg |
| Sterile, isotonic saline | 1000 mL |

The compound of the present invention is dissolved in the saline and administered intravenously at a rate of 1 mL per minute to a subject in need thereof.

FORMULATION 8

An aerosol solution is prepared by mixing the active ingredient with ethanol and then with the propellant 22, cooled to −30° C., and transferred to a filling device. The required amount is then fed to a stainless steel container and diluted with the remainder of the propellant. The value units are finally fitted to the container.

| Ingredient | Weight % |
| --- | --- |
| O-(3-[4-(2-fluorophenyl)-butylaminosulfonyl]benzyl-N-benzylcarbonyl-serine, free acid | 0.25 |
| Ethanol | 29.75 |
| Propellant 22 | 70.00 |
| Total | 100.00 |

EXAMPLES

Melting points were measured using a Thomas Hoover capillary instrument and are uncorrected. Ratios are on a weight basis, except fluid mixtures for chromatography, which are on a volume basis. Temperatures are in degrees Celsius. Chromatography was performed on silica under low or medium pressure "flash" conditions as described by C. W. Still, et al., *J. Org. Chem.* 43:2923 (1978). Thin layer Chromatography (TLC) was performed on glass plates coated with silica gel, 240 microns, grade 2.

Proton NMR spectra were obtained using a QE 300 at 300.15 MHz and peak positions are reported as delta values relative to an internal TMS standard.

The following abbreviations for common solvents, reagents and substituent groups are used throughout:

h, hour(s)
rt, room temperature (ca. 25°)
mM, millimole(s)
mL, millimeters
MeOH, methanol
EtOH, ethanol
THF, tetrahydrofuran
NaH, sodium hydride
DEAD, diethyl azodicarboxylate
DIAD, di-isopropyl azodicarboxylate
1-HOBT-NH$_3$, 1-Hydroxybenzotriazole-Ammonia Complex
EtOAc, ethyl acetate
HOAc, acetic acid
H$_2$O, water
H$_2$O$_2$, hydrogen peroxide
Na$_2$SO$_4$, sodium sulfate (anhydrous)
MgSO$_4$, magnesium sulfate (anhydrous)
NaOH, sodium hydroxide
HCl, hydrochloric acid
DCC, Dicyclohexyl carbodiimide
DMF, Dimethyl formamide
CH$_2$Cl$_2$, dichloromethane
CHCl$_3$, chloroform
Cbz, benzyloxycarbonyl
Bz, benzoyl
Ac, acetyl

Preparation 1

2-(2-Phenyl-4-oxazolyl)ethanol.

To an ice-cooled suspension of 5.87 g (0.155 mol) of LiAlH$_4$ in 700 mL of Et$_2$O was added a solution of 35.53 g (0.154 mol) of ethyl 2-phenyl-4-oxazoleacetate in 300 mL of Et$_2$O over a 1.5 hour period. The temperature of the reaction during the addition was kept below 15° C. After stirring for 2 hours at 25° C. the reaction was decomposed by the addition of 15 mL of EtOAc and 33.5 mL of water. The mixture was filtered through anhydrous $Na_2SO_4$ and concentrated in vacuo to leave 28.1 g of oil. Distillation of the crude oil gave 2-(2-phenyl-4-oxazolyl)ethanol (23.52 g, 81%, b.p. 120–122° C./0.05–0.06 mm) as an oil which solidified on standing.

Anal. Cal. for $C_{11}H_{11}NO_2$:C, 69.83; H, 5.86; N, 7.40
Found: C, 69.78; H, 5.90; N, 7.49

Preparation 2

3-[2-(2-Phenyl-4-oxazolyl)ethoxy]benzaldehyde.

10.00 g (81.89 mmoles) of triphenylphosphine were dried under vacuum and combined with 200 mL THF under $N_2$. The mixture was treated with 16.12 mL (81.89 mmoles) of diisopropylazodicarboxylate added dropwise over 0.25 hr resulting in a mild exotherm. After stirring for 24 hr at ambient temperature, the crude reaction mixture was concentrated under reduced pressure to a viscous amber oil. The oil was diluted in 300 mL EtOAc, washed with 2.5 N NaOH (3×200 mL), $H_2O$ (2×300), and brine 300 mL. The combined organics were dried over $MgSO_4$ and concentrated under reduced pressure again to a viscous amber oil. The reaction mixture was separated using silica gel column chromatography (6:1 Hex:EtOAc) from which the product was recovered and then recrystallized from iprOH to afford 15.10 g (63.10%.) of white crystalline solid, m.p. 51–53° C.

Anal: Cal. for $C_{18}H_{15}NO_3$: C, 73.70; H, 5.15; N, 4.77.
Found: C, 73.55; H ,5.07; N,4.53
H'NMR (DMSO-$d_6$)::3.05 (t,2H); 4.37 (t,2H); 7.35 (m,1H);
IR (Phase?):1696.6, 1595.3 $cm^{-1}$

EXAMPLE 1

O-[2-(2-Phenyl-4-oxazolyl)ethyl]-N-CBZ-L-tyrosine

Part A
Esterification of CBZ-L-Tyrosine.

CBZ-L-Tyrosine (18.9 g, 0.06 mol) (Aldrich) was added to 125 mL MeOH; the mixture was treated with 1 mL AcCl and stirred at RT for 24 h. The bulk of the MeOH was stripped, the residue dissolved in 200 mL EtOAc, and the solution washed successively with saturated $NaHCO_3$, $H_2O$, and brine. The solution was dried with $Na_2SO_4$ and evaporated to 19.4 g of a yellow oil, used directly in the next step.

Part B

A solution of 29.0 g (0.153 mol) of 2-(2-phenyl-4-oxazolyl)ethanol, 29.1 g (0.088 Mol) of the ester from part A, 23.7 g (0.090 Mol triphenyl phosphine and 350 mL THF was stirred under $N_2$. DEAD (15.7 g, 0.090 Mol) was added drop-wise over 5 h under autogenous temperature (slight exotherm). The reaction mixture was stirred at RT for 24 h, then treated with 0.5 mL of 30% $H_2O_2$. After stirring an additional 5 h, the mixture was concentrated in vacuo to a thick amber oil. The residue was taken up in 300 mL of EtOAc, the solution washed with $H_2O$, then with brine, and finally dried with $Na_2SO_4$. Residual EtOAC was removed in vacuo, the residue dissolved in 200 mL of MeOH, and the solution treated with 100 mL of 5N NaOH. After stirring overnight, the precipitate which had formed was removed by filtration. This recovered solid was CBZ-Tyrosine acid (14.7 g, 0.044 Mol). The filtrate was concentrated in vacuo, the residue dissolved in 200 mL EtOAC and the solution washed with three 50-mL portions of $H_2O$. The solution was reduced in volume to about 20 mL and applied to a 13 cm diameter column of 1 Kg of Silica Gel 60. Elution was begun with 1:1 Hexanes:EtOAC; 100% EtOAC eluted the impurities; final elution with 0.025% HOAc in EtOAC provided the product, which crystallized from MeOH to provide a semi-crystalline white solid (15.7 g, yield from 3 crops, 36.5% or 73.8% based on recovered CBZ-TyrOH).

mp. 105–111° C.
Anal.: Cal. for $C_{28}H_{26}N_2O_6$: C, 69.13; H, 5.39; N, 5.76
Found: C, 68.87; H, 5.24; N, 5.55
MS (FD): m/e 487;
IR (KBr): 3329, 1725, 1703 $cm^{-1}$
NMR (CDCl$_3$): 3.07 (t, 2H0, 3.12 (d, 2H), 4.24 (t, 2H), 4.67 (m, 1H), 5,12 (s, 2H), 5.25 (d, 1H), 6.83 (d, 2H), 7.07 (d, 2H), 7.35 (s, 5H), 7.46 (m, 3H), 7.58 (s, 1H), 8,02 (m, 2H)

EXAMPLE 2

O-[2-(2-Phenyl-4-oxazolyl)ethyl]-N-CBZ-L-tyrosine, sodium salt.

1.5 g (3.1 mM) of the free acid prepared in Example 1 were added to 40 mL of $H_2O$:MeOH (1:1). To this mixture was added drop-wise over 5 minutes 5 mL of an aqueous solution containing NaOH (0.185 g, 4.63 mM). The reaction mixture was stirred at ambient temperature for 15–20 minutes. The organic phase was then removed under reduced pressure and the remaining aqueous layer was diluted with 500 mL of EtOAc and washed with three 1 L portions of $H_2O$. The remaining organic layer was washed with 300 mL of brine, dried over $NaSO_4$, and stripped to a sticky white solid under reduced pressure. Overnight vacuum drying provided 0.508 g (1.00 mM, 32.5%) of the product.

mp 204–207°
Cal for $C_{28}H_{25}N_2O_6Na$: C, 66.14; H, 4.95; N, 5.51.
Found: C, 64.57; H, 5.22; N, 5.60.
I.R. (KBr): 3426, 1701, 1610 cm–1
HNMR (DMSO-d6): 2.81 (m, 1H), 2.98 (t, 2H), 3.07 (m, 1H), 3.95 (m, 1H), 4.11 (t, 2H), 4.95 (q, 2H), 6.80 (d, 2H), 7.09 (d, 2H), 7.29 (m, 5H), 7.52 (m, 3H), 7.95 (m, 2H), 8.02 (s, 1H)
MS: (IEX) molecular ion 508.9

EXAMPLE 3

O-[2-(2-Phenyl-4-oxazolyl)ethyl]-L-tyrosine.

Method A 5 g (10 mM) of the product described in Example 1 was added to 125 mL of dry dichloromethane and stirred at ambient temperature. To this solution, iodotrimethylsilane (8.78 mL, 61.6 mM) was added drop-wise over 10 minutes. The resulting mixture was stirred for 24 hrs. The reaction was quenched by slow addition of 50 mL of dry MeOH and stirred for 2–4 hrs. The solvent was then removed under reduced pressure resulting in a dark amber oil which was diluted with 100 mL MeOH treated with 15 mL 2.5 N NaOH, and stirred for 16 hrs in order to saponify the methyl ester. The reaction mixture was then concentrated, diluted with 300 mL 1:1 CHCl$_3$:water, and acidified with 5N HCl to pH~5–7. A white precipitate formed in the organic layer and was collected by vacuum filtration, washed with hot MeOH, and dried under vacuum to provide the product as a fine white powder (3.30 g, 9.36 mM, 91%).

mp 231–235° C.

Cal for $C_{20}H_{20}N_2O_4$: C, 68.17; H, 5.72; N, 7.95.

Found: C, 68.37; H, 5.90; N, 8.07.

I.R. (KBr): 1600 cm$^{-1}$

HNMR (DMSO-d$_6$/NaOD): 2.69–2.93 (m, 2H), 3.00 (t, 2H), 2.58–2.73 (m, 1H), 4.25 (t, 2H), 6.89 (d, 2H), 7.13 (d, 2H), 7.26 (d, 2H), 7.54 (m, 3H), 7.97 (m, 2H), 8.04 (s, 1H)

MS: (FAB+) M+1 ion 353.1

Method B

A solution of 5.0 gm of the product of Example 1 Part B in 100 mL THF was treated with 1.25 gm of 5% Pd/C catalyst and hydrogenated at RT overnight. The catalyst was removed by filtration and the solid slurried successively with 100 mL 2N NaOH and 50 mL 1 N NaOH. The combined alkaline extracts were refiltered and the filtrate adjusted to pH 4–5 with HOAc. The mixture was refrigerated 24h and filtered to provide white powder (2.4 gm, 66%).

mp 235–242 dec.

Anal.: Cal for $C_{20}H_{20}N_2O_4$: C, 68.17; H, 5.72; N, 7.95.

Found: C, 68.37; H, 5.90; N, 8.07.

EXAMPLE 4

O-[2-(2-Phenyl-4-oxazolyl)ethyl]-N-BZ-L-tyrosine.

5 g (14.19 mM) of the amino acid prepared in Example 4, Method A was combined with NaOH (2.83 mL, containing 70.9 mM), 150 mL of H$_2$O:dioxane (1:1), and 5 mg of phenolphthalein. The mixture was cooled to 0° C. Alternating drop-wise additions of benzoyl chloride (1.64 mL, 14.2 mM) and NaOH (2.5 N, about 0.6 mL, 1 eq) were made to maintain pH 9–10. The resulting mixture was stirred for 6 h at 0° C. and 16 h at ambient temperature.

The reaction mixture was concentrated, acidified to pH 1 and extracted 2× with 200 mL EtOAc, washed with 200 mL H2O, 200 mL brine, dried over NaSO$_4$, and concentrated again to a white sticky foam. The mixture was recrystallized from hot CHCl$_3$ providing white solid product (3.51 g, 54%).

mp 165–169° C.

Anal.: Cal for $C_{27}H_{24}N_2O_5$: C, 71.04; H, 5.30; N, 6.14.

Found: C, 70.85; H, 5.40; N, 5.88.

I.R. (KBr): 3278, 3061, 1712, 1645 cm$^{-1}$

HNMR (DMSO-d$_6$): 2.98 (t, 2H), 3.1 (m, 1H), 3.15 (m, 1H), 4.22 (t, 2H), 4.56 (m, 1H), 6.88 (d, 2H), 7.24 (d, 2H), 7.5 (m, 8H), 7.95 (m, 2H), 8.02 (s, 1H), 8.67 (d, 1H)

MS: (FD+) molecular ion 456.1

EXAMPLE 5

O-[2-(2-Phenyl-4oxazolyl)ethyl]-N-phenylacetyl-L-tyrosine

The procedure of Example 4 was followed, using phenylacetyl chloride in place of benzoyl chloride, to afford the product as a white solid (84% yield).

mp 146–151°

Anal: Cal. for $C_{28}H_{26}N_2O_5$: C, 71.48; H, 5.57; H, 5.95.

Found: C, 71.74; H, 5.63; N, 6.22.

IR(KBr): 3290, 1717, 1646 cm$^{-1}$

MS(FD+): m/e 471

NMR (DMSO-d$_6$): 2.79 (m, 2H), 3.00 (t, 2H), 4.23 (t, 2H), 4.38 (m, 1H), 6.84 (d, 2H), 7.10 (d, 2H), 7.19 (m, 5H), 7.54 (m, 3H), 7.97 (m, 2H), 8.04 (s, 1H), 8.33 (d, 2H), 12.69 (s, 1H)

EXAMPLE 6

O-[2-(2-Phenyl-4-oxazolyl)ethyl]-N-4-methylbenzoyl-L-tyrosine.

The procedure of Example 4 was followed, using para-methyl benzoyl chloride in place of benzoyl chloride, to provide the product a white solid after purification by chromatography (52% yield).

mp 180–182 °

Anal. Cal. for $C_{28}H_{26}O_5N_2$: C, 71.48; H, 5.57; N, 5.95

Found: C, 71.68; H, 5.70; N, 5.95.

IR(KBr): 3300, 1721, 1642 cm$^{-1}$

MS(FD): m/e 470

NMR (DMSO-d$_6$): 2.34 (s, 3H), 2.97 (t, 2H), 3.06 (m, 2H), 4.21 (t, 2H), 4.56 (m, 1H), 6.87 (d, 2H), 7.23 (m, 5H), 7.52 (m, 3H), 7.71 (d, 2H), 7.97 (m, 2H), 8.02 (s, 1H), 8.55 (d, 2H), 12.60 (bs, 1H)

EXAMPLE 7

4-[2-(2-phenyl-4-oxazolyl)ethoxy]benzyl-N-CBZ-L-serine.

Part A

4-[2-(2-phenyl-4-oxazolyl)ethoxy]benzaldehyde was first prepared following the procedures of Preparation 2 herein, using para-hydroxybenzaldehyde instead of 3-hydroxybenzalde. The aldehyde was reduced to 4-[2-(2-phenyl-4-oxazolyl)ethoxy]benzyl alcohol following the procedures of Example 22, Part A. A solution of 30.9 gm (0.10 mol) of 4-[2-(2-phenyl-4-oxazolyl)ethoxy]benzyl alcohol in 30 mL CH$_2$Cl$_2$ was treated with 10 mL of PBr$_3$ and kept at ambient temperature for 2 h. The solution was treated cautiously with 20 mL of MeOH and evaporated in vacuo. The residue was dissolved in EtOAc, the solution washed in sequence with cold H$_2$O, then 20% NaHCO$_3$, then H$_2$O, then brine, and finally dried over MgSO$_4$. Removal of solvent in vacuo afforded the solid bromide (24.5 g, 60 mM), used directly in Part B.

Part B 4.62 g (19.3 mM) of CBZ-L-Serine (Aldrich) as a 75 mL DMF solution was cooled to −5° C., treated with 1.7 g (42. mM) of 60% NaH in mineral oil, and stirred for 2–2.5 h. 8.3 g (23 mM) of the bromide prepared in Part A was added to this mixture drop-wise over 0.5 hr as a 75 mL DMF solution via cannula. The resulting mixture was stirred for 5 hr at −5° C. and was then allowed to warm slowly to ambient temperature, while stirring for 16 h. The solvent was then removed under reduced pressure and the residue was dissolved in 200 mL EtOAc, washed with 200 mL 1N HCL, 2× with 200 mL H$_2$O, then with brine, and finally dried over MgSO$_4$. The filtered solution was concentrated and purified by column chromatography using EtOAc:MeOH (15:2) containing 1% AcOH, and then recrystallized from EtOAc, to yield a white solid product (1.5 g, 87%, based on recovered starting material, otherwise 7%).

mp 124–126° C.

pc 499372

Cal for C$_{29}$H$_{28}$N$_2$O$_7$: C, 67.43; H, 5.46; N, 5.42.

Found: C, 68.58; H, 5,78; N, 5.22.

I.R.(KBr): 3321, 3127, 1689, 1609 cm$^{-1}$

H'NMR (DMSO-d6): 3.01 (t, 2H), 3.63 (m, 2H), 3.88 (m, 1H), 4.25 (t, 2H), 4.36 (s, 2H), 5.01 (s, 2H), 6.72 (m, 1H), 6.91 (d, 2H), 7.21 (d, 2H), 7.35 (m, 5H), 7.53 (m, 3H), 7.98 (m, 2H), 8.05 (s, 1H)

MS: (FD+) Molecular Ion 516.2

EXAMPLE 8

O-[2-(2-Phenyl-4-oxazolyl)ethyl]-N-methyl-N-CBZ-L-tyrosine

To 2 g (4 mM) of the product of Example 4, Part B was added 30 mL of dry THF and 0.5 mL of 15-crown-5. The mixture was cooled to 0° C. and 0.36 g of a 60% NaH/mineral oil dispersion was added (0.217 g/9.04 mM NaH) all at once and the resulting solution was stirred at 0° C. After approximately 1 h., methyl iodide (1.03 mL, 16.4 mM) was added drop-wise over 5 minutes, and the reaction was allowed to warm to ambient temperature and stir for 6 h. Five mL (~1 eq.) of 2 N HCl was added, and the reaction mixture was reduced to a dark yellow oil under reduced pressure. The residue was diluted with 200 mL of EtOAc, washed with 200 mL of 1 N HCl, then with 200 mL brine, and finally dried over NaSO$_4$. The dry solution was stripped to a yellow oil and purified by column chromatography, using a gradient starting with Hex:EtOAc (3:1) and ending with Hex:EtOAc (2.5:1) to give a clear oil (0.58 g, 37%).

Cal for C$_{29}$H$_{28}$N$_2$O$_6$: C, 69.59; H, 5.63; N, 5.60. Found: C, 69.66; H, 5.90; N, 5.43.

I.R. (KBr): 3621, 1740, 1996 cm$^{-1}$

HNMR (DMSO-d$_6$):2.70 (m, 2H)<3.00 (t, 2H), 3.65, 3.68 (ds, 3H), 4.22 (t, 2H), 4.84 (m, 1H), 4.96, 5.02 (dm, 2H), 6.85 (m, 2H), 7.06–7.35 (m, 7H), 7.53 (m, 3H), 7.97 (m, 2H) 8.04 (s, 1H)

MS: (FD+) Molecular ion 500

EXAMPLE 9

O-[2-(5-Methyl-2-phenyl-4-oxazolyl)ethyl]-N-CBZ-D, L-tyrosine

The procedure of Example 1, Part A was used to prepare 2-(5-methyl-2-phenyl-4-oxazolyl)ethanol from ethyl 5-methyl-2-phenyl-4-oxazoleacetate. 4-[2-(5-methyl-2-phenyl-4-oxazolyl)ethoxy] benzaldehyde was prepared following the procedures of Preparation 2, herein, using para-hydroxybenzaldehyde instead of 3-hydroxybenzaldehyde and 2-(5-methyl-2-phenyl-4-oxazolyl)ethanol instead of 2-(2-phenyl-4-oxazolyl)ethanol. The aldehyde was reduced to 4-[2-(5-methyl-2-phenyl-4-oxazolyl)ethoxy]benzyl alcohol following the procedures of Example 22, Part A. A solution of 3 gm (0.02 M) of 4-[2-(5-methyl-2-phenyl-4-oxazlyl)ethoxy]benzyl alcohol in 30 mL CH$_2$Cl$_2$ was treated with 1 mL of PBr$_3$ and kept at ambient temperature for 2 h. The solution was treated cautiously with 2 mL of MeOH and evaporated in vacuo. The residue was dissolved in EtOAc, the solution washed with cold H$_2$O, then with 20% NaHCO$_3$, then with H$_2$O, then with brine, and finally dried over MgSO$_4$. Removal of solvent in vacuo afforded the solid bromide (2 g, 6 mM). The solid bromide was dissolved in 20 mL THF and and the solution was added drop-wise to a solution prepared by the reaction of 0.42 g of 60% NaH/oil dispersion (10 mM NaH), 1.6 gm (5.2 mM) of N-CBZ Diethylaminomalonate hydrochloride and 30 mL of EtOH. The subsequent reaction was allowed to proceed at ambient temperature for 12 h, during which time a precipitate had formed. TLC demonstrated the consumption of starting materials. The mixture was treated with 20 mL H$_2$O and NaOH (1.1 g), stirred, and heated to reflux for 1 h. The cooled mixture was acidified to pH 2, diluted with H$_2$O and extracted with EtOAc. The combined EtOAc extracts were washed with H$_2$O, thwn with brine, and finally dried with MgSO$_4$. Removal of solvent afforded a yellow taffy which crystallized from EtOAc/Hexane to provide the product as a white powder (0.78 g, 16% overall).

mp 142–143°.

Anal.: Cal. for C$_{29}$H$_{28}$N$_2$O: C, 69.59; H, 5.64; N, 5.60 Found: C, 69.86; H, 5.67; N, 5.31

MS: m/e 500

IR (KBr): 3374, 1730, 1646 cm$^{-1}$

NMR ($_{CDC_{13}}$): 2.4 (s, 3H), 3.0 (t, 2H), 3.1 (d, 2H), 4.2 (t, 3H), 4.65 (m, 1H), 5.1 (s, 2H), 5.3 (d, 1H, exchanges with D$_2$O), 6.9 (d, 2H), 7.1 (d, 2H), 7.2–7.5 (m, 8H), 7.95 (m, 2H)

EXAMPLE 10

O-[2-(2-Phenyl-4-oxazolyl)ethyl]-N-CBZ-L-tyrosine Carboxamide 2 g (4.11 mmoles) of the product of Example 1 was added to 30 mL of dry DMF and cooled to 0° C. 0.933 g (4.52 mmoles) of solid DCC were added all at once to the cold reaction which was stirred for another 15 minutes at 0° C. Finally, 0.688 g (4.52 mmoles) of HOBT.NH$_3$ was added and the reaction mixture was allowed to stir at 0° C. for 1 h, and then at ambient temperature for 2 h. The solution was concentrated, diluted with 300 mL H$_2$O, extracted 3× with 200 mL EtOAc, washed with 300 mL brine, and finally dried over NaSO$_4$. The extracts were filtered and concentrated to small volume and chilled to −10° C. for 16 h. and the precipitate formed was collected and dried to provide a white solid product (1.4 g, 70%).

mp 180–181° C.;

Cal for C$_{28}$H$_{27}$N$_3$O$_5$: C, 69.27; H, 5.61; N, 8.65. Found: C, 69.41; H, 5.41; N, 8.64

I.R. (KBr): 3424, 3312, 3198, 1658 cm$^{-1}$

HNMR (CDCl$_3$): 2.95 (m, 2H), 3.10 (t, 2H), 4.27 (t, 2H), 4.37 (m, 1H), 5.10 (s, 2H), 5.30 (bs, 2H), 5.62 (bs, 1H), 6.86 (d, 2H), 7.14 (d, 2H), 7.33 (m, 5H), 7.45 (m, 3H), 7.58 (s, 1H), 8.03 (m, 2H)

MS: (FD) molecular ion 485

EXAMPLE 11

O-[2-(2-Phenyl-4-oxazolyl)ethyl]-N-CBZ-L-tyrosine Hydroxamic Acid

Four grams (7.77 mM) of the product of Example 1 and 5.40 g (77.7 mM) of hydroxylamine hydrochloride were dissolved in 100 mL MeOH and treated with an aqueous solution of potassium carbonate (50 mL, 116.6 mM, 16.11 g). The resulting mixture was stirred at ambient temperature for 3 h. The solvent was then removed under reduced pressure at ~35° C. The remaining solid was triturated 3× with 75 mL H$_2$O, filtered, dried, dissolved in 20 mL of hot DMF and diluted with ~100 mL diethyl ether. A white powdery product was recovered from the chilled solution (1.5 g, 38%).

mp 198–199° C.;

Cal for C$_{28}$H$_{27}$N$_3$O$_6$: C, 67.05; H, 5.43; N, 8.38. Found: C, 66.85; H, 5.53; N, 8.28.

I.R. (KBr): 3290, 3213, 1690 cm$^{-1}$

HNMR (DMSO-d$_6$): 2.65–2.85 (m, 2H), 3.00 (t, 2H), 4.05 (m, 1H), 4.23 (t, 2H), 4.93 (s, 2H), 6.87 (d, 2H), 7.17 (m, 2H), 8.04 (s, 1H), 8.85 (s, 1H), 10.69 (s, 1H)

MS: (FD) molecular ion 501

EXAMPLE 12

O-[2-(2-Phenyl-4-oxazolyl)ethyl]-N-phenoxyacetyl-L-tyrosine

The procedure of Example 4 was followed, using phenoxyacetyl chloride in place of benzoyl chloride, to provide the product as a white solid (84% yield).

mp 94–97°

Anal. Cal. for C$_{28}$H$_{26}$N$_2$O$_6$: C, 69.12; H, 5.39; N, 5.76 Found: C, 68.88; H, 5.39; N, 5.66

IR(KBr): 1713, 1664 cm$^{-1}$

MS(FD+): m/e 487

NMR (DMSO-d$_6$): 3.00 (m, 4H), 4.24 (t, 2H), 4.46 (s, 2H), 6.85 (d, 2H), 6.93 (t, 3H), 7.12 (d, 2H), 7.25 (t, 2H), 7.54 (m, 3H), 7.97 (m, 2H), 8.04 (s, 1H), 8.19 (d, 2H), 12.84 (s, 1H)

EXAMPLE 13

O-[2-(2-Phenyl-4-oxazolyl)ethyl]-N-4-chlorobenzoyl-L-tyrosine

The procedure of Example 4 was followed, using 4-chlorobenzoyl chloride in place of benzoyl chloride, to provide the product as a white solid (95% yield).

mp 158–161°

Anal. Cal. for C$_{29}$H$_{23}$ClN$_2$O$_5$: C, 66.06; H, 4.72; N, 5.71. Found: C, 65.79; H, 4.66; N, 5.88.

IR(KBr): 3294, 1729, 1661 cm$^{-1}$

MS(FD): m/e 491

NMR(DMSO-d$_6$/CDCl$_3$):3.07 (t, 2H), 3.17 (dd, 1H), 4.25 (t, 2H), 4.91 (m, 1H), 6.84 (d, 2H), 7.13 (m, 3H), 7.59 (s, 1H), 7.71 (d, 2H), 8.04 (m, 2H)

EXAMPLE 14

O-[2-(2-Phenyl-4-oxazolyl)ethyl]-N-phenylmethylsulfonyl-L-Tyrosine.

The procedure of Example 4 was followed, using phenylmethyl sulfonyl chloride in place of benzoyl chloride, to provide the product as a white solid (74% yield).

mp 141–143°

Anal. Cal. for C$_{27}$H$_{26}$N$_2$O$_6$S: C, 64.02; H, 5.17; N, 5.53. Found: C, 64.00; H, 5.09, N, 5.31.

IR(KBr): 1701 cm$^{-1}$

MS(FD+): m/e 507

NMR(DMSO-d$_6$): 2.74 (dd, 1H), 2.93 (dd, 1H), 2.98 (t, 2H), 3.90–4.13 (m, 3H), 4.25 (t, 2H), 6.91 (d, 2H), 7.16 (m, 4H), 7.27 (m, 3H), 7.51 (m, 3H), 7.60 (d, 1H), 7.95 (m, 2H), 8.00 (s, 1H), 12.78 (bs, 1H).

EXAMPLE 15

O-[2-(1-Naphthyl)ethyl]-N-CBZ-L-tyrosine

The procedure of Example 1, Part C was followed, using 2-(1-naphthyl)ethanol in place of 2-(2-phenyl-4-oxazolyl) ethanol, to provide the a white solid product after purification by column chromatography (13% yield).

mp 80–83°

Anal. Cal. for C$_{29}$H$_{27}$NO$_5$: C, 74.18; H, 5.80; N, 2.98. Found: C, 73.94; H, 5.71; N, 2.88.

IR(KBr): 3319, 1698 cm$^{-1}$

MS(FD): m/e 470

NMR (CDCl$_3$): 3.08 (m, 2H), 3.55 (t, 2H), 4.13 (m, 1H), 4.23 (t, 2H), 5.50 (dd, 2H), 5.19 (d, 1H), 6.78 (d, 2H), 7.03 (d, 2H), 7.30 (m, 5H), 7.40 (m, 2H), 7.49 (m, 2H), 7.76 (m, 1H), 7.86 (m, 1H), 8.08 (m, 1H).

EXAMPLE 16

O-[2-(2-Phenyl-4-oxazolyl)ethyl]-N-(4-bromobenzyloxycarbonyl)-L-tyrosine

Part A (4-Bromobenzyl)-(4-nitrophenyl) carbonate was prepared by the methods of Letsinger, R. L. and Ogilvie, K. K.; *J. Org. Chem.* (1967), 32, 296, or that of Kugel, C., Lellouche, J. -P., and Beaucourt, J. -P., *Tetrahedron Lett.* (1989), 30, 4947.

To an anhydrous dichloromethane (200 mL) solution of 4-nitrophenyl chloroformate (9.02 g, 45 mmole) under nitrogen at 5° C. was added drop-wise a dichloromethane (100 mL) solution of 4-bromobenzyl alcohol (8.79 g, 47 mmole, 1.04 eq) and pyridine (7.3 mL, 90 mmole, 2 eq). After 1 hour, the reaction was allowed to warm to room temperature. After 2 hours, TLC with dichloromethane:hexane (4:1) showed no starting alcohol. The dichloromethane was washed with 1 N HCl (3×100 mL), brine (2×150 mL), dried (MgSO$_4$), filtered, and evaporated in vacuo to give 15.7 g of a white solid. Triturated in ether/hexane, filtered and dried to give 13.29 g (84%) of product.

mp: 121–123° C.

$^1$H NMR (CDCl$_3$): δ5.24 (2H, s); 7.32 (2H, d, J=8 Hz); 7.37 (2H, d, J=9 Hz); 7.55 (2H, d, J=8 Hz); 8.27 (2H, d, J=9 Hz)

MS: MW=352.14, observed (FD, MeOH) 351, 353

IR(CHCl$_3$): 1529, 1767

EA:

Anal. Calcd for C$_{14}$H$_{10}$BrNO$_5$: C, 47.75; H, 2.86; N, 3.98. Found: C, 48.00; H, 2.97; N, 4.11.

Part B

To an anhydrous DMF (170 mL) suspension of O-[2-(2-phenyl-4-oxazolyl)ethyl-L-tyrosine (previously described in Example 4, Method A) (4.93 g, 14 mmole) under nitrogen was added cesium carbonate (18.25 g, 56 mmole, 4 eq). After cooling to 5° C., the mixture was treated with 4-bromobenzyl 4-nitrophenylcarbonate (4.93 g, 14 mmole, 1 eq). After 10 minutes, the ice bath was removed and the reaction stirred for 1.5 hours. The reaction was cooled to 5° C., iodomethane (2.1 mL, 34 mmole, 2.4 eq) was added and the reaction was allowed to warm to room temperature over 16 hours. The mixture was poured into water/EtOAC (500 mL/500 mL). The layers were separated and the aqueous layer was mixed with brine and extracted with EtOAc (4×250 mL). The combined EtOAc portions were washed with 1 N HCl (250 mL), dried (MgSO$_4$), filtered and evaporated in vacuo to provide 12.14 g of an orange oil. The oil was purified on a Waters Prep 2000 LC liquid chromatograph using a gradient of hexane:EtOAc (9:1) to hexane:EtOAc (1:1) to provide 3.7 g (53%) of a yellow oil. NMR and FD indicate contamination with N-methylated material.

EA:

Anal. Calcd for $C_{29}H_{27}BrN_2O_6$: C, 60.11; H, 4.70; N, 4.83. Found: C, 60.26; H, 4.87; N, 4.78.

$^1$H NMR (CDCl$_3$): δ3.09 (4H, m); 3.72 (3H, s); 4.26 (2H, t, J=6.5 Hz); 4.60 (1H, m); 5.03 (2H, s); 5.20 (NH, d, J=8 Hz); 6.83 (2H, d, J=8.5 Hz); 6.99 (2H, d, J=8.5 Hz); 7.19 (2H, d J=8 Hz); 7.45 (5H, m); 7.57 (1H, s); 8.02 (2H, m)

MS: MW=579.45, observed (FD, MeOH) 578, 580 second set at 590, 592 for +Me

To a MeOH (200 mL) suspension of the above product (3.7 g, 6.4 mmole) cooled to 5° C. was added 1 N NaOH (7.7 mL, 1.2 eq). The mixture was allowed to come slowly to room temperature with stirring for 24 hours. TLC using hexane:1 EtOAc (1:1) showed starting material still present. More 1 N NaOH (1.3 mL, 0.2 eq) was added and stirring was continued for 18 hours. A majority of the MeOH was removed in vacuo and the resulting residue partitioned between 1 N HCl/EtOAc (100 mL/250 mL). The layers were separated and the aqueous was washed with EtOAc (2×100 mL). The combined EtOAc portions were washed with brine (2×250 mL), dried (Mg SO$_4$), filtered and evaporated in vacuo to provide 3.7 g. Recrystallized from MeOH to provide 1.76 g. Recrystallized again from EtOAc/hexane to provide 1.20 g (33%).

mp: 173–176° C.

EA:

Anal. Calcd for $C_{28}H_{25}BrN_2O_6$: C, 59.48; H, 4.46; N, 4.95. Found: C, 59.75; H, 4.62; N, 5.05.

$^1$H NMR (DMSO): δ2.71 (1H, m); 2.96 (3H, m); 4.08 (1H, m); 4.19 (2H, t, J=6.5 Hz); 4.90 (2H, s); 5.03 (2H, s); 6.83 (2H, d, J=8.5 Hz); 7.12 (2H, d, J=8.5 Hz); 7.16 (2H, d, J=8 Hz); 7.47 (5H, m); 7.62 (NH, d, J=8 Hz); 7.92 (2H, m); 8.00 (1H, s); 12.73 (OH, bs)

MS: MW=565.42, observed (FD, MeOH) 564, 566

IR(KBr): 1694, 1738, 3322

EXAMPLE 17

O-[2-(2-Phenyl-4-oxazolyl)ethyl]-N-(4-trifluoromethylbenzyloxycarbonyl)-L-Tyrosine Part A. Preparation of (4-Trifluoromethylbenzyl)-(4-nitrophenyl) Carbonate.

In a manner similar to Example 17, Part A, 4-nitrophenyl chloroformate (10.08 g, 50 mmole) was treated with 4-(trifluoromethyl)benzyl alcohol (7.2 mL, 52.5 mmole, 1.05 eq) and pyridine (8.1 mL, 100 mmole, 2 eq). Trituration in ether provided 11.87 g (70%) of a white solid.

mp: 95.5–96.5° C.

EA:

Anal. Calcd for $C_{15}H_{10}F_3NO_5$: C, 52.80; H, 2.95; N, 4.11. Found: C, 52.94; H, 2.94; N, 4.20.

$^1$H NMR (CDCl$_3$): δ5.35 (2H, s); 7.39 (2H, d, J=9 Hz); 7.57 (2H, d, J=8 Hz); 7.68 (2H, d, J=8 Hz); 8.28 (2H, d, J=9 Hz)

MS: MW=341.24, observed (FD, MeOH) 341

IR(CHCl$_3$): 1530, 1768

Part B

To an anhydrous DMF (150 mL) suspension of O-[2-(2-phenyl-4-oxazolyl)ethyl-L-tyrosine (previously described in Example 4, Method B) (3.14 g, 8.4 mmole) under nitrogen was added cesium carbonate (10.95 g, 33.6 mmole, 4 eq). After cooling to 5° C. the mixture was treated with 4-(trifluoromethyl)benzyl 4-nitrophenylcarbonate (3.44 g, 10.1 mmole, 1.2 eq). After 10 minutes the ice bath was removed and the reaction stirred for 24 hours. Some of the DMF was removed in vacuo and the remainder was poured into 1 N HCl (500 mL). Washed with EtOAc (4×200 mL). The combined EtOAc portions were washed with brine (2×200 mL), dried (MgSO$_4$), filtered, and evaporated in vacuo to provide 9.8 g of a brown oil. The oil was purified on a Waters Prep 2000 LC liquid chromatograph using a gradient of hexane:EtOAc (9:1) to EtOAc over 10 minutes. 100% EtOAc was run for 5 minutes, and then a further gradient to EtOAc:MeOH/2%AcOH (95:5) was run over 10 minutes to provide 2.27 g. Recrystallization from EtOAc/hexane provided 1.65 g (35%) of a white solid.

mp: 177–180.5° C.

EA:

Anal. Calcd for $C_{29}H_{25}F_3N_2O_6$: C, 62.81; H, 4.54; N, 5.05. Found: C, 63.09; H, 4.65; N, 5.22.

$^1$H NMR (d$_6$-DMSO): δ2.72 (1H, m); 2.95 (3H, m); 4.09 (1H, m); 4.19 (2H, t, J=6.5 Hz); 5.03 (2H, s); 6.84 (2H, d, J=8.5 Hz); 7.13 (2H, d, J=8.5 Hz); 7.40 (2H, d, J=8 Hz); 7.47 (3H, m); 7.65 (2H, d, J=8 Hz); 7.69 (NH, d, J=8.5 Hz); 7.92 (2H, m); 8.00 (1H, s); 12.74 (OH, bs)

MS: MW=554.52, observed (FD, MeOH) 554

IR(CHCl$_3$): 1513, 1722, 3430

EXAMPLE 18

O-[2-(2-Phenyl-4-oxazolyl)ethyl]-N-(4-methoxybenzyloxycarbonyl)-L-tyrosine

Part A

In a manner similar to Example 17, Part A 4-nitrophenyl chloroformate (10.8 g, 50 mmole) was treated with 4-methoxybenzyl alcohol (6.6 mL, 52.5 mmole, 1.05 eq) and pyridine (8.1 mL, 100 mmole, 2 eq). Trituration in ether/hexane provided 13.83 g (91%) of a white solid.

mp: 106–107° C.

EA: Anal. Calcd for $C_{15}H_{13}NO_6$: C, 59.41; H, 4.32; N, 4.62. Found: C, 59.70; H, 4.42; N, 4.71.

$^1$H NMR (CDCl$_3$): δ3.83 (3H, s); 5.24 (2H, s); 6.93 (2H, d, J=8.5 Hz); 7.37 (2H, d, J=9 Hz); 7.39 (2H, d, J=8.5 Hz); 8.27 (2H, d, J=9 Hz)

MS: MW=303.27, observed (FD, MeOH) 303

Part B

An anhydrous DMF (170 mL) suspension of O-[2-(2-phenyl-4-oxazolyl)ethyl-L-tyrosine (previously described in Example 4, Method A) (4.93 g, 14 mmole) under nitrogen was treated with cesium carbonate (13.68 g, 42 mmole, 3 eq) and 4-methoxybenzyl 4-nitrophenylcarbonate (4.25 g, 14 mmole, 1 eq) in a manner similar to Example B and provided 14.57 g of an orange oil. The oil was purified on a Waters Prep 2000 LC liquid chromatograph to provide 3.60 g of an oily, yellow solid. Recrystallization from CH$_2$Cl$_2$/hexane provided 1.03 g (15%) of a white solid.

mp: 132.5–135.5° C.

EA: Anal. Calcd for C$_{29}$H$_{28}$N$_2$O$_7$: C, 67.43; H, 5.46; N, 5.42. Found: C, 67.74; H, 5.54; N, 5.31.

$^1$H NMR (d$_6$-DMSO): δ2.71 (1H, m); 2.95 (3H, m); 3.68 (3H, s); 4.06 (1H, m); 4.19 (2H, t, J=6.5 Hz); 4.84 (2H, s); 6.83 (4H, m); 7.11 (2H, d, J=8 Hz); 7.17 (2H, d, J=8 Hz); 7.47 (4H, m); 7.92 (2H, m); 7.99 (1H, s); 12.70 (OH, bs)

MS: MW=516.55, observed (FD, MeOH) 517

IR (CHCl$_3$): 1514, 1717, 2962, 3432

EXAMPLE 19

O-[2-(2-Phenyl-4-oxazolyl)ethyl]-N-(4-n-Butylbenzyloxycarbonyl)-L-tyrosine

Part A

In a manner similar to Example 17, Part A 4-nitrophenyl chloroformate (10.08 g, 50 mmole) was treated with 4-butylbenzyl alcohol (9 mL, 52.5 mmole, 1.05 eq) and pyridine (8.1 mL, 100 mmole, 2 eq). Evaporation in vacuo provided 15.57 g (95%) of a light yellow oil.

EA: Anal. Calcd for C$_{18}$H$_{19}$NO$_5$: C, 65.64; H, 5.82; N, 4.25. Found: C, 65.45; H, 5.62; N, 4.48.

$^1$H NMR (CDCl$_3$): δ0.93 (3H, t, J=7 Hz); 1.38 (2H, m); 1.61 (2H, m); 2.64 (2H, J=8 Hz); 5.27 (2H, s); 7.22 (2H, d, J=8 Hz); 7.36 (2H, d, J=8 Hz); 7.38 (2H, d, J=9 Hz); 8.27 (2H, d, J=9 Hz)

MS: MW=329.36, observed (FD, MeOH) 329

IR(CHCl$_3$): 1529, 1766, 2933, 2961

Part B

An anhydrous DMF (170 mL) suspension of O-[2-(2-phenyl-4-oxazolyl)ethyl-L-tyrosine (previously described in Example 4, Method B, used as the HCl salt) (4.99 g, 12.8 mmole) under nitrogen was treated with cesium carbonate (14.52 g, 45 mmole, 3.5 eq) and 4-butylbenzyl 4-nitrophenylcarbonate (4.82 g, 14.1 mmole, 1.1 eq) in a manner similar to Example B and provided 10.55 g of a brown oil. The brown oil was purified on Waters Prep 2000 LC liquid chromatograph to provide 2.28 g solid. Recrystallization from ether/hexane and drying provided 1.33 g (19%) of a yellow solid.

mp: 86–89° C.

EA: Anal. Calcd for C$_{32}$H$_{34}$N$_2$O$_6$: C, 70.83; H, 6.32; N, 5.16. Found: C, 70.58; H, 6.42; N, 5.40.

$^1$H NMR (d$_6$-DMSO): δ0.82 (3H, t, J=7 Hz); 1.21 (2H, m); 1.46 (2H, m); 2.49 (2H, t, J=7.5 Hz); 2.70 (1H, m); 2.96 (3H, m); 3.68 (3H, s); 4.08 (1H, m); 4.19 (2H, t, J=6.5 Hz); 4.87 (2H, s); 6.82 (2H, d, J=8.5 Hz); 7.10 (6H, m); 7.47 (3H, m); 7.53 (NH, d, J=8.5 Hz); 7.92 (2H, m); 7.99 (1H, s); 12.68 (OH, bs)

MS: MW=542.63, observed (FD, MeOH) 542

IR(CHCl$_3$): 1513, 1717, 2961, 3432

EXAMPLE 20

O-[2-(2-Phenyl-4-oxazolyl)ethyl]-N-(N'-Benzylcarbamoyl)-L-tyrosine

The method described in Arrieta, A. and Palomo, C., *Synthesis* (1982) 1050 was followed to prepare O-[2-(2-Phenyl-4-oxazolyl)ethyl]-N-(N'-Benzyl) carbamoyl-L-tyrosine. To a partial THF (100 mL) solution of O-[2-(2-phenyl-4-oxazolyl)ethyl-L-tyrosine (previously described in Example 4, Method B, used as the HCl salt) (3.89 g, 10 mmole) under nitrogen was added 1,1,1,3,3,3-hexamethyldisilazane (2.11 mL, 10 mmole, 1 eq) and stirred for 30 minutes. Benzylisocyanate (1.24 mL, 10 mmole, 1 eq) was added, and stirred for 16 hours. The volume of THF was reduced in half and water/EtOAc (100 mL/500 mL) was added to precipitate out an insoluble solid. The biphasic mixture was filtered and dried under vacuum to provide 1.84 g of a tan solid. Recrystallization from MeOH provided 1.28 g (26%) of product.

mp: 196.5–198° C.

EA:

Anal. Calcd for C$_{28}$H$_{27}$N$_3$O$_5$: C, 69.26; H, 5.60; N, 8.65. Found: C, 69.00; H, 5.69; N, 8.90.

$^1$H NMR (d$_6$-DMSO): δ2.75 (1H, m); 2.88–2.98 (3H, m); 4.12 (2H, d, J=6 Hz); 4.12 (2H, t, J=6.5 Hz); 4.29 (1H, m); 6.08 (NH, d, J=8 Hz); 6.50 (NH, t, J=6 Hz); 6.83 (2H, d, J=8 Hz); 7.04 (2H, d, J=8 Hz); 7.15 (3H, m); 7.24 (2H, m); 7.48 (3H, m); 7.92 (2H, m); 8.00 (1H, s); 12.59 (OH, bs)

MS: MW=485.54, observed (FD, MeOH) 485

IR(KBr): 1555, 1636, 1737, 3276, 3375

EXAMPLE 21

α-(3-[2-(2-phenyl-4-oxazolyl)ethoxy]benzyl)-N-CBZ Glycine

Part A

Preparation of 3-[2-(2-phenyl-4-oxazolyl)ethoxy]benzyl alcohol 14.0 g (47.9 mM) of 3-[2-(2-phenyl-4-oxazolyl)ethoxy] benzaldehyde, prepared as described in Preparation 2 herein, was diluted with 200 mL i-PrOH and treated with 2.89 g (76.6 mM) of sodium borohydride. The mixture was stirred at ambient temperature for 24 hr. 250 mL of H$_2$O was added slowly over a period of 1 hr to quench the reaction and the resulting mixture was stirred for 1 hr. It was then concentrated under reduced pressure and the residue was diluted with 300 mL EtOAc and washed with H$_2$O (300 mL) and brine (300 mL). All the organics were combined, dried over MgSO$_4$, and concentrated to yield 13.6 g of a yellow waxy solid.

m.p. 59–62° C., 96.5%.

E.A. Cal. for $C_{18}H_{17}NO_3$ (MW 295): C, 73.20; H, 5.80; N, 4.74. Found: C, 73.42; H, 5.83; N, 5.01.

H'NMR: (DMSO-$D_6$) 3.02 (t, 2H); 3.61 (broad s, 1H); 4.27 (t, 2H); 4.46 (d, 2H), 6.80–6.95 (m, 3H) 7.23 (t, 1H); 7.55 (m, 3H) 7.98 (m, 2H); 8.05 (s, 1H)

IR: 1600, 1552, 3269 $cm^{-1}$

MS (FD+) 295

Part B

Preparation of 3-[2-(2-phenyl-4-oxazolyl)ethoxy]benzyl bromide 15.8 g (53.5 mM of 3-[2-(2-phenyl-4-oxazolyl)ethoxy] benzyl alcohol was dried under vacuum, diluted with 300 mL $Et_2O$ and cooled to 0° C. The solution was treated with 5.59 mL (58.8 mM) phosphorus tribromide added dropwise over 5–10 min and stirred for 6–8 hr at 0° C. 20 mL of MeOH was added over 20 minutes and the resulting mixture was stirred 1 hr at 0° C. The solvent was removed under reduced pressure and the residue was diluted with 300 mL $CHCl_3$ and washed with $H_2O$ (300 mL) and brine (300 mL). The organics were concentrated, the residue was recrystallized from $Et_2O$ and 14.1 g of the product was collected.

m.p. 73–75° C., 73.6%.

E.A.

Cal. for $C_{18}H_{16}BrNO_2$ (MW 358): C, 60.35; H, 4.50; N, 3.91. Found: C, 60.12; H, 4.55; N, 3.94.

H'NMR: (DMSO-$D_6$) 3.02 (t, 2H); 4.27 (t,2H); 4.67 (s, 2H); 6.94 (m, 1H) 7.05 (m, 2H), 7.29 (m, 1H); 7.54 (m, 3H) 7.98 (m, 2H); 8.06 (s, 1H)

IR: 1597.26, 1554.82 $cm^{-1}$

MS (FD+) 356

Part C.

A solution of NaOEt in EtOH, prepared from 30 mL EtOH and 0.6 g of 60% NaH/oil (15.0 mM of NaH) was treated with 3.1 g (8.7 mM) 3-[2-(2-phenyl-4-oxazolyl)ethoxy] benzyl bromide. The resulting pale yellow solution was treated dropwise with a solution of 3.0 g (9.7 mM) of N-CBZ Diethylamino malonate in 30 mL THF over 0.25 h. The faintly turbid mixture was stirred at ambient temperature 4 h, treated with 2.8 g (70 mM) NaOH, 20 mL $H_2O$ and heated to reflux 2 h. The mixture was acidified to pH ca. 3 and allowed to cool under $N_2$. After 12 h, the mixture was partially concentrated in vaccuo, diluted with 250 mL $H_2O$ and extracted with a total of 200 mL EtOAc in 3 portions. The combined extracts were washed with $H_2O$, brine, dried with $MgSO_4$ and evaporated. The residual pale yellow taffy slowly solidified on trituration with small portions of hexane. Recrystallization from THF-cyclohexane provide the product as a nearly white soft powder, 2.47 g (58%), mp 149–151° C. dec (gas).

Anal. Cal. for $C_{28}H_{26}N_2O_6$ (MW 486):

C, 69.12; H, 5.39; N, 5.76.

Found: C, 69.34; H, 5.65; N, 5.67.

NMR: 3.0 (m, 2H), 3.1 (t, 2H), 4.2–4.4 (overlapping t, d, 4H), 4.7 (d, 2H), 5.1 (m, 1H), 6.9 (dd, 1H), 7.15 (d, 1H), 7.3. (m, 1H), 7.45 (m, 3H), 7.6 (s, 1H), 8.05 (m, 2H)

IR(KBr) 3326, 1729, 1690, 1596 $cm^{-1}$

MS(FD) m/e 486

EXAMPLE 22

O-[2-(5-Methyl-2-phenyl-4-oxazolyl)ethyl]-N-CBZ-L-tyrosine

Following the procedure of Example 1, Part C, the condensation of 2-(5-Methyl-2-phenyl-4-oxazolyl)ethanol with 8.10 g of the ester from Example 1, Part A, followed by saponification afforded 4.25 g (34.5%) of the product as a white powder.

mp 75–95° C.

Anal.: Cal for $C_{29}H_{28}N_2O_6 \cdot H_2O$: C, 67.17; H, 5.83; N, 5.40. Found: C, 67.34; H, 5.68; N, 5.55.

MS m/e

IR(KBr) 1717 $cm^{-1}$

NMR (DMSO-$d_6$): 2.40 (s, 3H), 2.64 (m, 2H), 2.79 (t, 2H), 3.89 (m, 1H), 4.05 (t, 2H), 4.84 (m, 2H), 2.64 (d, 2H), 6.99 (d, 2H), 7.04–7.23 (m, 5H), 7.38 (m, 3H), 7.81 (m, 3H), 12.75 (broad s, 1H).

EXAMPLE 23

O-[2-(5-Methyl-2-phenyl-4-oxazolyl)ethyl]-N-BZ-tyrosine

The procedure of Example 9 is followed, substituting N-benzoyl-diethylaminomalonate for N-CBZ-benzoyl-diethylaminomalonate.

EXAMPLE 24

O-(3-[2-(2-Phenyl-4-oxazolyl)ethoxy]benzyl)-N-CBZ serine 0.448 g of 60% NaH/oil (0.27 g, 11.1 mM of NaH) was added to 40 mL of dry THF and cooled to 0° C. 1.21 g (5.08 mM of CBZ-serine was added dropwise as a dry DMF solution (10 mL) over 5 minutes. The resulting mixture was stirred at 0° C. for 1 hr. 2.00 g (5.58 mmoles) of 3-[2-(2-phenyl-4-oxazolyl)ethoxy]benzyl bromide, prepared as described in Example 22, Part B, was also added dropwise as a dry DMF solution (10 mL) over 5 minutes. The final mixture was stirred for 5 h at 0° C and was then allowed to warm to ambient over 12 h. The reaction was quenched with 20 mL of methanol and one equivalent of HCl. After concentrating to a small volume under reduced pressure, the mixture was diluted with 200 mL EtOAc, washed with 200 mL water (2×) and 200 mL brine. The organic phase was dried over $MgSO_4$, filtered and concentrated to a yellow, opaque oil. The product was purified using silica column chromatography, (25:5:1 $CHCl_3$:MeOH:$NH_4OH$>>>3:4 MeOH:EtOAc), and recrystallized from $Et_2O$. to provide 714 mg 49.6%) of product as a white, waxy solid.

mp. 55–57° C.

E.A Cal. for $C_{29}H_{28}N_2O_7$: C, 67.43; H, 5.46; N, 5.42. Found C, 67.70; H, 5.74; N, 5.48.

H'NMR: (DMSO-$D_6$) _3.00 (t, 2H); _4.27 (t,2H); _4.27 (m,1H); _4.45 (s,2H); _5.04 (s, 2H); 6.90 (m,3H) _7.20–_ 8.05 (s,1H); _12.60–13.00 (broad s, 1H)

IR (KBr): 1759.30, 1685.04, 3313.16 $cm^{-1}$

MS (FD+) m/e 517

EXAMPLE 25

N-Benzyloxycarbonyl-O-(4-(2-(2-Phenyloxazol-4-yl)ethoxy)phenyl)methyl-L-Serine

Preparation of O-Methanesulfonyl-2-Phenyl-4-Hydroxyethyloxazole

To a solution of 2-phenyl-4-hydroxyethyloxazole (60 g, 317 mmol) in 600 mL of methylene chloride at 5° C under a nitrogen atmosphere was added triethylamine (62 mL, 444 mmol) and methanesulfonyl chloride (30.7 mL, 396 mmol). The resulting solution was allowed to stir at 5° C. for 1.5 hours before extracting the reaction mixture with 10% aqueous ammonium chloride (2×500 mL). The organics remaining were dried over magnesium sulfate and the solvent was removed to give 86.4 g of the title compound as an oil that was used directly in the next step.

Yield: >100%. $^1$H NMR. 98.9% pure by HPLC (Zorbax SB-CN, 25 cm, 1 mL/min, 50:50 acetonitrile: 1% aqueous ammonium acetate).

Preparation of O-Benzaldehyd-4-yl-2-Phenyl-4-Hydroxyethyloxazole

Methanesulfonyl-2-phenyl-4-hydroxyethyloxazole (2.0 g, 7.5 mmol), 4-hydroxybenzaldehyde (830 mg, 6.8 mmol), and cesium carbonate (2.44 g, 7.5 mmol) in 15 mL of dimethylformamide were heated to 45° C. for 8 hours. The progress of the reaction was monitored by HPLC (Zorbax SB-CN, 25 cm, 1 mL/min, 50:50 acetonitrile: 1% aqueous ammonium acetate). The reaction was cooled and diluted with 75 mL of ethyl acetate. The mixture was washed with water and 10% aqueous ammonium chloride (2×75 mL) and then the combined aqueous extracts were back extracted with 25 mL of ethyl acetate. The combined organics were dried over magnesium sulfate, filtered, and the solvent was removed. The residue was recrystallized from 20 mL of 3:1 hexanes: ethyl acetate to give 1.49 g of the title compound.

Yield: 75%. $^1$H NMR. 96.9% pure by HPLC (Zorbax SB-CN, 25 cm, 1 mL/min, 50:50 acetonitrile: 1% aqueous ammonium acetate).

$^1$H NMR (300 MHz, DMSO-d$_6$) 9.813 (s, 1H), 8.008 (s, 1H), 7.893–7.924 (m, 2H), 7.809 (d, 2H, J=8.72 Hz), 7.455–7.488 (m, 3H), 7.110 (d, 2H, J=8.72 Hz), 4.345 (t, 2H, J=6.55 Hz), 2.999 (t, 2H, J=6.55 Hz); $^{13}$C NMR (75 MHz, DMSO-d$_6$) 191.188, 163.287, 160.364, 138.176, 136.259, 131.739, 130.433, 129.971, 129.679, 129.041, 128.690, 126.897, 125.782, 124.906, 124.884, 114.930, 66.235, 25.973. IR (KBr) v 3127, 2838, 1693, 1678, 1600, 1580, 1553, 1509, 1490, 1460, 1447, 1393, 1311, 1252, 1214, 1164, 1158, 1114, 1099, 1063, 1031, 934, 898, 832, 814, 780, 722, 708, 690, 665, 651, 618 cm$^{-1}$. UV (EtOH) λ 276 (ε33580), λ 214 (ε19126).

MS (FD) m/z 293 (M$^+$, 100%).

Anal. calc'd for C$_{18}$H$_{15}$NO$_3$ C, 73.71; H, 5.15; N, 4.77. Found C, 73.75; H, 5.12; N, 4.77.

Preparation of 2-Phenyl-4-(4-Hydroxymethylphenoxy)ethyloxazole

To a solution of O-benzaldehyd-4-yl-2-phenyl-4-hydroxyethyloxazole (62.33 g, 212 mmol) in 620 mL of isopropanol at room temperature was added sodium borohydride (16.08 g, 424 mmol). The resulting solution was allowed to stir for about 16 hours. The progress of the reaction was monitored by HPLC (Zorbax SB-CN, 25 cm, 1 mL/min, 50:50 acetonitrile: 1% aqueous ammonium acetate). Deionized water (870 mL) was added and the slurry was stirred for 30 minutes before filtering through a felt filter pad using 3.5 L of water as a rinse. The product filter cake weighed 61.73 g.

Yield: 98%. 99.6% pure by HPLC (Zorbax SB-CN, 25 cm, 1 mL/min, 50:50 acetonitrile: 1% aqueous ammonium acetate). $^1$NMR (300 MHz, DMSO-d$_6$ 7.981 (s, 1H), 7.897–7.929 (m, 2H), 7.443–7.478 (m, 3H), 7.171 (d, 2H, J=8.54 Hz), 6.864 (d, 2H J=8.54 Hz), 5.003 (t, 1H, J=5.74 Hz), 4.358 (d, 2H, J=5.74 Hz), 4.197 (t, 2H, J=6.63), 2.946 (t, 2H, J=6.63 Hz); $^{13}$C NMR (75 MHz, DMSO-d$_6$) 160.307, 157.200, 141.072, 138.488, 136.140, 134.695, 130.405, 129.043, 127,879, 126.934, 126.658, 125.781, 124.898, 114.099, 65.730, 62.518, 26.192. IR (KBr) v 1612, 1599, 1510, 1448, 1295, 1243, 1223, 1045, 1033, 812, 710, 690 cm$^{-1}$. UV (EtOH) λ 271 (ε19115), λ 220 (ε15003). MS (FD) m/z 295 (M$^+$, 100%).

Anal calc'd for C$_{18}$H$_{17}$NO$_3$ C, 73.20; H, 5.80; N, 4.74. Found C, 72.95H, 5.59N, 4.65

Preparation of 2-Phenyl-4-(4-Bromomethylphenoxy)ethyloxazole

To a suspension of 2-phenyl-4-(4-hydroxymethylphenoxy)ethyloxazole (30 g, 102 mmol) in 300 mL of methylene chloride at 5° C under a nitrogen atmosphere was added phosphorous tribromide (10.02 mL, 107 mmol) dropwise keeping the temperature of the reaction below 20° C. The resulting solution was allowed to stir for about 2 hours at room temperature. The reaction was cooled to about 10° C and 20 mL of methanol was added. After about 5 minutes, the solvent was removed and the solid remaining was partitioned between 1.35 L of ethyl acetate and 1.05 L of cold 5% aqueous sodium bicarbonate. The organics were washed with another 1.05 L of 5% aqueous sodium bicarbonate, dried over magnesium sulfate, filtered, and removed to give 33.3 g of the title compound.

Yield: 92%. $^1$H NMR. TLC (2:1 hexanes: ethyl acetate): 1 spot.

Preparation of N-Trityl-O-(4-(2-(2-Phenyloxazol-4-yl)ethoxy)phenyl)methyl-L-Serine Methyl Ester To a mixture of 2-phenyl-4-(4-bromomethylphenoxy)ethyloxazole (55.67 g, 155 mmol), N-trityl-L-serine methyl ester (51.06 g, 141 mmol), and tetrabutylammonium bromide (45.54 g, 141 mmol) in 950 mL of methylene chloride was added aqueous sodium hydroxide (37.3 mL, 705 mmol). The resulting mixture was heated at a gentle reflux for about 24 hours. The progress of the reaction was monitored by HPLC (Zorbax SB-CN, 25 cm, 1 mL/min, 50:50 acetonitrile: 1% aqueous phosphoric acid). The reaction was diluted with 1 L of methylene chloride and washed with water (3×2 L). The organics were dried over magnesium sulfate, filtered, and removed to give 115.7 g of a crude product oil which was used in subsequent reactions without further purification.

Yield: <100%. 67% pure by HPLC (Zorbax SB-CN, 25 cm, 1 mL/min, 50:50 acetonitrile: 1% aqueous phosphoric acid).

Preparation of N-Benzyloxycarbonyl-O-(4-(2-(2-Phenyloxazol-4-yl)ethoxy)phenyl)methyl-L-Serine Methyl Ester To a solution of crude N-trityl-O-(4-(2-(2-phenyloxazol-4yl)ethoxy)phenyl)methyl-L-serine methyl ester (115.8 g, 141 mmol) in 860 mL of 1:1 diethyl ether:methanol at about 5° C. was added hydrochloric acid (1 M in diethyl ether, 353 mL, 353 mmol) dropwise over about 20 minutes. Once the addition was complete, the reaction was allowed to stir at 5° C. for 45 minutes. The progress of the reaction was monitored by HPLC (Zorbax SB-CN, 25 cm, 1 mL/min, 60:40 acetonitrile: 1% aqueous phosphoric acid). The solvent was removed in vacuo and the residue was partitioned between 2.5 L of diethyl ether and 750 mL of water. The ether layer was washed (3×250 mL) with deionized water and the combined aqueous extracts were back extracted with 500 mL of diethyl ether. The pH of the aqueous extracts was adjusted to about 8 with sodium bicarbonate (47.5 g) and then 750 mL of ethyl acetate and benzyloxycarbonyl chloride (22.2 mL, 155 mmol) were added. The reaction was allowed to stir at room temperature for 45 minutes before removing the ethyl acetate layer. The aqueous layer was back extracted with 1.5 L of ethyl acetate and then combined ethyl acetate layers were dried over magnesium sulfate, filtered, and removed to give 60.91 g of crude product which was used in subsequent reactions without further purification.

Yield: 81%. 78% pure by HPLC (Zorbax SB-CN, 25 cm, 1 mL/min, 60:40 acetonitrile: 1% aqueous phosphoric acid). $^1$H NMR (300 MHz, DMSO-$d_6$) 7.985 (s, 1H), 7.898–7.929 (m, 2H), 7.736 (d, 1H, J=8.0 Hz), 7.456–7.491 (m, 3H), 7.250–7.311 (m, 5H), 7.166 (d, 2H, J=8.55 Hz), 6.878 (d, 2H, J=8.55 Hz), 4.993 (s, 2H), 4.344 (d, 2H, J=1.64 Hz), 4.286–4.312 (m, 1H), 4.208 (t, 2H, J=6.58 Hz), 3.295–3.599 (m, 5H), 2.952 (t, 2H, J=6.58 Hz); $^{13}$C MNR (75 MHz, DMSO-$d_6$) 170.731, 160.311, 157.842, 156.001, 138.458, 136.845, 136.178, 130.422, 129.976, 129.181, 120.055, 128.278, 127.759, 127.662, 126.937, 125.781, 124.907, 114.222, 92.556, 71.690, 68.555, 65.740, 65.537, 54.120, 51.935, 26.158. IR (KBr) v 3311,1735, 1688, 1539, 1516, 1301, 1269, 1248, 1208, 1177, 1078, 1036, 1002, 783 cm$^{-1}$. UV (EtOH) λ271 (ε17739). MS (FD) m/z 530 (M$^+$, 100%). Anal calc'd for $C_{30}H_{30}N_2O_7$ C, 67.91; H, 5.70; N, 5.28 Found C, 67.92; H, 5.70; N, 5.19

Preparation of N-Benzyloxycarbonyl-O-(4-(2-(2-Phenyloxazol-4-yl)ethoxy)phenyl)methyl-L-Serine To a solution of crude N-benzyloxycarbonyl-O-(4-(2-(2-phenyloxazol-4-yl)ethoxy)phenyl)methyl-L-serine methyl ester (13.32 g, 25.1 mmol) in 133 mL of tetrahydrofuran at 2° C. was added 44 mL of deionized water. A solution of lithium hydroxide (1.2 g, 50.2 mmol) in 40 mL of deionized water was added slowly over 25 minutes keeping the temperature of the reaction below 4° C. After the addition was complete the reaction was allowed to stir at 2° C. for 1 hour. The pH of the mixture was adjusted to about 1 with 6 N hydrochloric acid (8.3 mL). Water (130 mL) was added and the reaction was extracted with ethyl acetate (2×260 mL). The organic extracts were dried over magnesium sulfate, filtered, and the solvent removed to give an oil that was solvent exchanged into 125 mL of acetonitrile. The product crystallized and the slurry was stirred for about 1 hour at about 2° C. The precipitate was filtered using filtrete and rinsed with cold acetonitrile to give 7.65 g of the title compound.

Yield: 59%. 98.6% pure, 98.9% ee by HPLC. $^1$H NMR (300 MHz, DMSO-$d_6$) 12.707 (s, 1H), 7.990 (s, 1H) 7.896–7.928 (m, 2H), 7.542 (d, 1H, J=8.22 Hz), 7.458–7.480 (m, 3H), 7.249–7.311 (m, 5H), 7.178 (d, J=8.47), 6.870 (d, 2H, J=8.47 Hz), 4.984 (s, 2H), 4.344 (s, 2H), 4.161–4.227 (m, 3H), 3.587 (d, 2H, J=4.51 Hz), 2.950 (t, 2H, J=6.52 Hz); $^{13}$C NMR (75 MHz, DMSO-$d_6$) 171.645, 160.310, 157.805, 156.015, 138.460, 136.938, 136.180, 130.425, 130.090, 129.198, 120.059, 128.266, 127.723, 127.641, 126.936, 125.785, 114.201, 92.563, 71.707, 68.896, 65.734, 65.432, 54.159, 26.158. IR (KBr) v 3313,1690, 1609, 1532, 1513, 1277, 1264, 1250, 1077, 1061, 1031, 688 cm$^{-1}$. UV (EtOH) λ271 )(ε19449). MS (FD) m/z (M$^+$, 100%).
Anal calc'd for $C_{29}H_{28}N_2O_7$ C, 67.43; H, 5.46; N, 5.42. Found C, 67.31; H, 5.26; N, 5.35.

Male obese-diabetic viable yellow ($C^{vy}$) mice were divided into two groups of 6 each. One group was fed repelletized Purina 5008 Chow and the second group was fed a repelletized chow consisting of Purina 5008 Chow, admixed with varying doses of the candidate compound. Blood samples were taken before the experiment was initiated and 14 days after initiation. Body weight and food consumption were monitored. The blood glucose levels after 14 days of treatment was measured and recorded as a percent of the initial value, compared to the untreated control (first) group. The results are presented in the table below and include the dose of the candidate compound as a weight percent in the amount incorporated into the diet. The positive control is a known hypoglycemic agent (*J. Med. Chem.* 35:2617, 1992) administered in the same way as a compound of the present invention.

TABLE 1

Serum glucose levels after 14 days of administration of compounds of the Formula I.

| Compound Administered | Dose mg/100 g food | Serum Glucose after 14 days % of day 0 value |
|---|---|---|
| Example No. 1 | 0.03 | 49 |
| Example No. 2 | 0.03 | 67 |
| Example No. 4 | 0.03 | 60 |
| Example No. 5 | 0.03 | 57 |
| Example No. 6 | 0.03 | 65 |
| Example No. 7 | 0.03 | 34 |
| Example No. 8 | 0.06 | 75 |
| Example No. 9 | 0.03 | 66 |
| Example No. 10 | 0.03 | 88 |
| Example No. 21 | 0.03 | 48 |
| Example No. 22 | 0.03 | 53 |
| Example No. 24 | 0.01 | 88 |
| (positive control) | 0.003 | 29 |

In the same study feeding study described above, plasma triglycerides were measured against a glycerol standard using reagents from Sigma Kit No. 339 (St. Louis, Mo.), adapted for assay on the Monarch System (Instrumentation Laboratory, Lexington, Mass.). Day 14 levels are recorded below as mM of triglycerides per mL. Serum triglyceride values for untreated animals averaged about 4 mmol/mL.

TABLE 2

Serum triglyceride levels after 14 days of administration of compounds of the Formula I.

| Compound Administered | Dose (mg/100 g food) | Serum Triglyceride after 14 days (nmol/mL) |
|---|---|---|
| Example No. 1 | 0.03 | 1.3 |
| Example No. 2 | 0.03 | 3.3 |
| Example No. 4 | 0.03 | 1.5 |
| Example No. 6 | 0.03 | 2.3 |
| Example No. 7 | 0.03 | 0.4 |
| Example No. 8 | 0.03 | 3.6 |

TABLE 2-continued

Serum triglyceride levels after 14 days of administration of compounds of the Formula I.

| Compound Administered | Dose (mg/100 g food) | Serum Triglyceride after 14 days (nmol/mL) |
| --- | --- | --- |
| Example No. 9 | 0.03 | 2.5 |
| Example No. 21 | 0.03 | 1.4 |
| Example No. 24 | 0.01 | 0.3 |
| clofibric acid (positive control) | 0.10 | 1.9 |

What is claimed is:

1. A compound of formula I

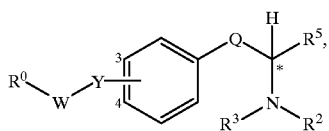

(I)

wherein:

Q is selected from the group consisting of —(CH$_2$)$_p$— and —CH$_2$—O—CH$_2$—;

R$^0$ is the group

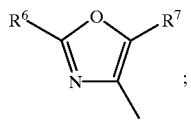

;

R$^2$ is selected from the group consisting of C$_{1-4}$ alkylaminocarbonyl, arylcarbonyl, aryloxycarbonyl, aryloxy C$_{1-4}$ arlylcarbonyl, arylaminocarbonyl, aryl C$_{1-4}$ acyl, aryl C$_{1-4}$ alkoxycarbonyl, aryl C$_{1-4}$ alkylaminocarbonyl, aryl C$_{1-4}$ akylsulfonyl, and amino-protecting groups;

R$^3$ is hydrogen, or C$_{1-4}$ alkyl;

R$^5$ is —COOH, —CONR$^{10}$R$^{11}$, —CN, —CONHOH, or

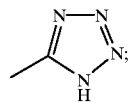

;

R$^6$ is hydrogen, C$_{1-4}$ alkyl, aryl, or aryl C$_{1-4}$ alkyl;

R$^7$ is hydrogen, halogen, or C$_{1-4}$ alkyl;

R$^{10}$ or R$^{11}$ are independently hydrogen, C$_{1-4}$ alkyl, or aryl;

W is —(CH$_2$)$_n$—;

Y is attached at position 3 or at position 4, and is —O—;

n is 1 to 4; and p is 1, 2, or 3;

or a pharmaceutically-acceptable salt thereof;

provided that when R$^6$ is either hydrogen or C$_{1-4}$ alkyl, then R$^7$ is halogen.

2. The compound of claim 1, wherein Q is —CH$_2$—O—CH$_2$—.

3. The compound of claim 2, wherein

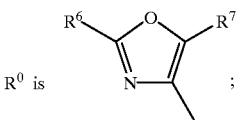

R$^0$ is ;

R$^2$ is arylcarbonyl, aryloxycarbonyl, arylaminocarbonyl, aryl C$_{1-4}$ arlkyloxycarbonyl, aryloxy C$_{1-4}$ alkylcarbonyl, or aryl C$_{1-4}$ alkylsulfonyl;

R$^3$ is hydrogen or methyl;

R$^5$ is —COOH, —CONR$^{10}$R$^{11}$, or

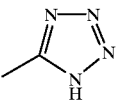

R$^6$ is aryl;

R$^7$ is hydrogen, halogen, or methyl;

R$^{10}$ and R$^{11}$ are hydrogen; and

Y is —O— —S—.

4. The compound of claim 3, wherein

R$^0$ is

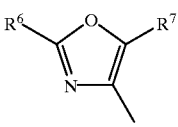

R$^2$ is arylcarbonyl, aryloxycarbonyl, aryl C$_{1-4}$ alkoxycarbonyl, or aryl C$_{1-4}$ alkylsulfonyl;

R$^5$ is —COOH;

R$^7$ is hydrogen, fluoro, or methyl;

Y is —O—; and n is 1 to 2.

5. The compound of claim 4, wherein

R$^0$ is

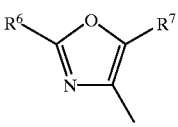

;

R$^2$ is benzyloxycarbonyl, phenylcarbonyl, benzylcarbonyl, methylbenzylcarbonyl, phenyloxycarbonyl, para-chlorophenylcarbonyl, benzylsulfonyl, para-bromophneylcarbonyl, para-trifluoromethylphenyloxycarbonyl, para-methoxyphenyloxycarbonyl, para-n-butylphenyloxycarbonyl, or phenyloxymethylcarbonyl, benzlyaminocarbonyl;

R$^6$ is phenyl;

R$^7$ is hydrogen;

Y is attached at the 4 position; and n is 2.

6. The compound of the formula

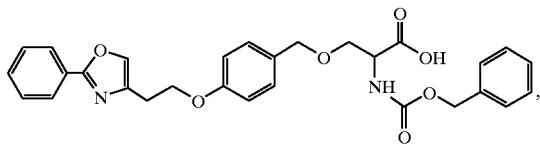

or a pharmaceutically acceptable salt thereof.
7. The compound of claim 1, wherein Q is $(CH_2)_p$.
8. The compound of claim 7, wherein p is 3.
9. The compound of claim 7, wherein p is 2.
10. The compound of claim 7, wherein p is 1.
11. The compound of claim 10, wherein $R^0$ is 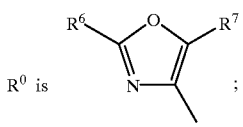 ;

$R^2$ is arylcarbonyl, aryloxycarbonyl, arylaminocarbonyl, aryl $C_{1-4}$ alkoxycarbonyl, aryloxy $C_{1-4}$ alkylcarbonyl, or aryl $C_{1-4}$ alkylsulfonyl;
$R^3$ is hydrogen or methyl;
$R^5$ is —COOH, —CONR$^{10}$R$^{11}$, or

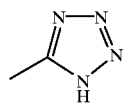

$R^6$ is aryl;
$R^7$ is hydrogen, halogen, or methyl;
$R^{20}$ and $R^{11}$ are hydrogen; and
Y is —O— or —S—.
12. The compound of claim 11, wherein
$R^0$ is

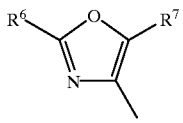

$R^2$ is arylcarbonyl, aryloxycarbonyl, aryl $C_{1-4}$ alkoxycarbonyl, or aryl $C_{1-4}$ alkylsulfonyl;
$R^5$ is —COOH;
$R^7$ is hydrogen, fluoro, or methyl;
Y is —O—; and
n is 1 or 2.
13. The compound of claim 12, wherein
$R^0$ is

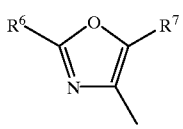

$R^2$ is benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, or phenyloxymethylcarbonyl, benzylaminocarbonyl;
$R^6$ is phenyl;
$R^7$ is hydrogen;
Y is attached at the 4 position; and
N is 2.
14. The compound of the formula

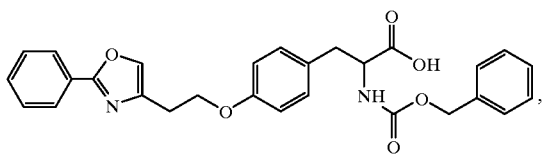

or a pharmaceutically acceptable salt thereof.
15. The compound of claim 1, wherein Y is attached at the 4 position of the ring.
16. The compound of claim 1, wherein Y is attached at the 3 position of the ring.
17. The compound of claim 1, which is the R enantiomer.
18. The compound of claim 1, which is the S enantiomer.
19. The compound of claim 1, which is the racemate.
20. A pharmaceutical formulation comprising as an active ingredient a compound of formula (I), as climaxed in claim 1, together with one or more pharmaceutically-acceptable excipients.
21. A pharmaceutical formulation comprising the compound of claim 6, or a pharmaceutically-acceptable salt thereof, together with one or more pharmaceutically-acceptable excipients.
22. A pharmaceutical formulation comprising the compound of claim 14, or a pharmaceutically-acceptable salt thereof, together with one or more pharmaceutically-acceptable excipients.
23. A method of treating hyperglycemia comprising administering to a mammal an effect dose of the compound of claim 1.
24. A method of treating hyperglycemia comprising administering to a mammal an effective dose of the compound of claim 6.
25. A method of treating hyperglycemia comprising administering to a mammal an effective dose of the compound of claim 14.
26. A method of treating hyperlipidemia comprising administering to a mammal an effective dose of the compound of claim 1.
27. A method of treating hyperlipidemia comprising administering to a mammal an effective dose of the compound of claim 6.
28. A method of treating hyperlipidemia comprising administering to a mammal an effective dose of the compound of claim 14.

29. A process for producing a compound of the formula

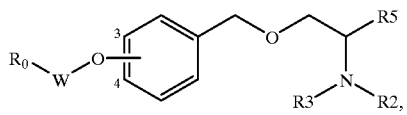

wherein:

$R^0$ is selected from the group consisting of

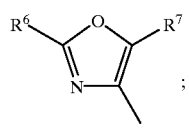

$R^2$ is selected from the group consisting of $C_{1-4}$ alkylaminocarbonyl, arylcarbonyl, aryloxycarbonyl, arloxy $C_{1-4}$ alkylcarbonyl, arylaminocarbonyl, aryl $C_{1-4}$ acyl, aryl $C_{1-4}$ alkoxycarbonyl, aryl $C_{1-4}$ alkylaminocarbonyl, aryl $C_{1-4}$ alkylsulfonyl and amino protecting groups;

$R^3$ is hydrogen, or $C_{1-4}$ alkyl;

$R^5$ is —COOH, —CONR$^{10}$R$^{11}$, —CONHOH, or

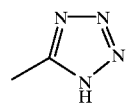

$R^6$ is hydrogen, $C_{1-4}$ alkyl, aryl, or aryl $C_{1-4}$ alkyl;

$R^7$ is hydrogen, halogen or $C_{1-4}$ alkyl;

$R^{10}$ and $R^{11}$ are independently hydrogen, $C_{1-4}$ alkyl, or aryl;

W is $(CH_2)_n$—;

n is 1 to 4; and the oxygen bonded to the group W is also bonded to the ring at position 3 to position 4 of the ring; or a pharmaceutically-acceptable salt thereof; provided that when $R^6$ is either hydrogen or $C_{1-4}$ alkyl, then $R^7$ is halogen, comprising A. combining a compound of formula

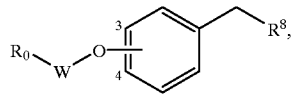

wherein $R^8$ is an activated hydroxy group, and wherein the oxygen bonded to the group W is bonded to the ring at position 3 to position 4 of the ring, with a compound of the formula

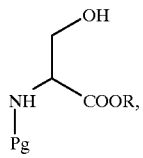

wherein R is a carboxy protecting group and Pg is an amino protecting group, in the presence of a phase transfer catalyst, under conditions permitting reaction to form a compound of formula

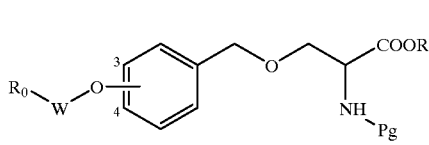

B. deprotecting the protected carboxy group of the compound of formula (XI) to produce a compound of the formula

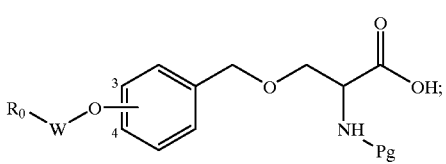

C. optionally converting the carboxy group of the compound of formula (XII) to

CONR$^{10}$R$^{11}$, —CN, —CONHOH, or

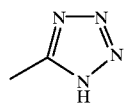

D. optionally replacing the amino protecting group (Pg) protecting the amino group of the compound of formula (XII) with $C_{1-4}$ alkylaminocarbonyl, arylcarbonyl, aryloxycarbonyl, aryloxy $C_{1-4}$ alkylcarbonyl, arylaminocarbonyl, aryl $C_{1-4}$ acyl, aryl $C_{1-4}$ alkoxycarbonyl, aryl $C_{1-4}$ alkylaminocarbonyl, aryl $C_{1-4}$ alkylsulfonyl or a different amino protecting group to form a compound of formula

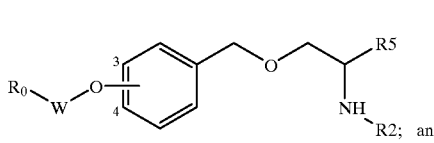

E. optionally alkylating the amino group of the compound of formula (XIII) to form a compound of formula

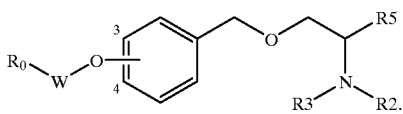

30. A process for making a compound of the Formula I

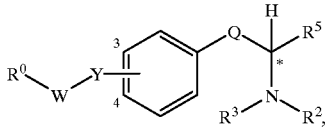 (I)

wherein:

Q is selected from the group consisting of —(CH$_2$)$_p$— and —CH$_2$—O—CH$_2$—;

R$^0$ is selected from the group consisting of

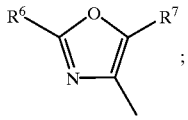 ;

R$^2$ is selected from the group consisting of C$_{1-4}$ alkylaminocarbonyl, arylcarbonyl, arlyoxycarbonyl, aryloxy C$_{1-4}$ alkylcarbonyl, arylaminocarbonyl, aryl C$_{1-4}$ acyl, aryl C$_{1-4}$ alkoxycarbonyl, aryl C$_{1-4}$ alkylaminocarbonyl, aryl C$_{1-4}$ alkylsulfonyl, and amino-protecting groups;

R$^3$ is hydrogen, or C$_{1-4}$ alkyl;

R$^5$ is —COOH, —CONR$^{10}$R$^{11}$, —CN, —CONHOH, or

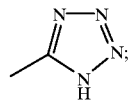

R$^6$ is hydrogen, C$_{1-4}$ alkyl, aryl, or aryl C$_{1-4}$ alkyl;

R$^7$ is hydrogen, halogen, or C$_{1-4}$ alkyl;

R$^{10}$ and R$^{11}$ are independently hydrogen, C$_{1-4}$ alkyl, or aryl;

W is (CH$_2$)$_n$—;

Y is attached at position 3 or at position 4, and is —O—;

n is 1 to 4; and p is 1, 2, or 3;

or a pharmaceutically-acceptable salt thereof; provided that when R$^6$ is either hydrogen or C$_{1-4}$ alkyl, then R$^7$ is halogen, and that when p=1, then R$^0$ is

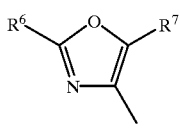

or a pharmaceutically-acceptable salt thereof, comprising:

A. reacting a compound of the formula

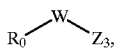

wherein Z3 is —OH, —SO$_2$Cl, a halogen leaving group, —NHR$^9$, or —COCl, with a compound of the formula

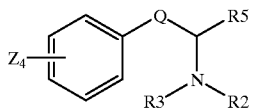

wherein Z4 is —OH, —SH, —NH$_2$, or —SO$_2$Cl, to form a compound of the formula (I); or B. deprotecting a compound of the formula

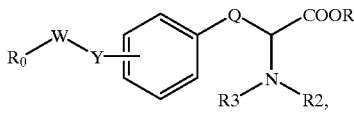

wherein R is a carboxy protecting group, to form a compound of formula (I) wherein R5 is a free carboxy group.

* * * * *